United States Patent
Genkin et al.

(10) Patent No.: US 10,617,743 B2
(45) Date of Patent: Apr. 14, 2020

(54) METHOD TO IMPROVE SAFETY AND EFFICACY OF ANTI-CANCER THERAPY

(71) Applicant: CLS Therapeutics Limited, St. Peter Port OT (GG)

(72) Inventors: Dmitry Dmitrievich Genkin, St. Petersburg (RU); Georgy Viktorovich Tets, St. Petersburg (RU); Viktor Veniaminovich Tets, St. Petersburg (RU)

(73) Assignee: CLS THERAPEUTICS LIMITED, Guernsey, Channel Islands (GB)

(*) Notice: Subject to any disclaimer, the term of this patent is extended or adjusted under 35 U.S.C. 154(b) by 459 days.

(21) Appl. No.: 15/530,666

(22) Filed: Jun. 19, 2015

(65) Prior Publication Data

US 2018/0071370 A1    Mar. 15, 2018

Related U.S. Application Data

(60) Provisional application No. 62/014,341, filed on Jun. 19, 2014.

(51) Int. Cl.

| A61K 38/46 | (2006.01) |
|---|---|
| A61K 9/00 | (2006.01) |
| A61K 31/704 | (2006.01) |
| A61K 31/7048 | (2006.01) |
| A61K 31/337 | (2006.01) |
| A61K 31/513 | (2006.01) |
| A61K 31/675 | (2006.01) |

(52) U.S. Cl.
CPC .......... *A61K 38/465* (2013.01); *A61K 9/0053* (2013.01); *A61K 31/337* (2013.01); *A61K 31/513* (2013.01); *A61K 31/675* (2013.01); *A61K 31/704* (2013.01); *A61K 31/7048* (2013.01); *C12Y 301/21* (2013.01); *C12Y 301/21001* (2013.01)

(58) Field of Classification Search
CPC .............. A61K 38/465; A61K 2300/00; A61K 9/0053; A61K 31/00; A61K 9/0019; C12Y 301/21; C12Y 301/21001; C12Y 301/22001
See application file for complete search history.

(56) References Cited

U.S. PATENT DOCUMENTS

| 3,224,942 A | 12/1965 | Martin |
|---|---|---|
| 4,485,095 A | 11/1984 | Fujisaki et al. |
| 5,484,589 A | 1/1996 | Salganik |
| 5,656,589 A | 8/1997 | Stossel et al. |
| 5,830,744 A | 11/1998 | Rosen et al. |
| 5,855,920 A | 1/1999 | Chein |
| 5,889,153 A | 3/1999 | Suzuki et al. |
| 5,952,170 A | 9/1999 | Stroun et al. |
| 6,033,846 A | 3/2000 | Fournie |
| 6,156,504 A | 12/2000 | Gocke et al. |
| 6,391,607 B1 | 5/2002 | Lazarus et al. |
| 6,428,785 B1 | 8/2002 | Gokcen |
| 6,455,250 B1 | 9/2002 | Aguilera et al. |
| 6,465,177 B1 | 10/2002 | Hoon |
| 6,521,409 B1 | 2/2003 | Gocke et al. |
| 7,402,724 B2 | 7/2008 | Conover |
| 7,612,032 B2 | 11/2009 | Genkin et al. |
| 8,388,951 B2 | 3/2013 | Genkin et al. |
| 8,535,663 B2 | 9/2013 | Genkin et al. |
| 8,710,012 B2 | 4/2014 | Genkin et al. |
| 8,759,004 B2 | 6/2014 | Coy |
| 8,796,004 B2 | 8/2014 | Genkin et al. |
| 8,871,200 B2 | 10/2014 | Genkin et al. |
| 2003/0044403 A1 | 3/2003 | Shak |
| 2004/0001817 A1 | 1/2004 | Giampapa |
| 2004/0157239 A1 | 8/2004 | Tanuma et al. |
| 2006/0228347 A1 | 10/2006 | Sunaga et al. |
| 2006/0233780 A1 | 10/2006 | Genkin et al. |
| 2007/0104702 A1 | 5/2007 | Genkin et al. |
| 2008/0004561 A1 | 1/2008 | Genkin et al. |
| 2009/0047272 A1 | 2/2009 | Appelbaum et al. |
| 2009/0053200 A1 | 2/2009 | Genkin et al. |
| 2010/0061971 A1 | 3/2010 | Genkin et al. |
| 2010/0150903 A1 | 6/2010 | Genkin et al. |
| 2010/0303796 A1 | 12/2010 | Genkin et al. |
| 2011/0033438 A1 | 2/2011 | Bartoov et al. |
| 2011/0070201 A1 | 3/2011 | Shaaltiel et al. |
| 2011/0189156 A1 | 8/2011 | Genkin et al. |
| 2012/0252750 A1 | 10/2012 | Shea et al. |
| 2013/0183283 A1 | 7/2013 | Genkin et al. |
| 2013/0183284 A1 | 7/2013 | Genkin et al. |
| 2013/0209443 A9 | 8/2013 | Genkin et al. |
| 2013/0216516 A1 | 8/2013 | Genkin et al. |

(Continued)

FOREIGN PATENT DOCUMENTS

| CA | 2184582 A1 | 9/1995 |
|---|---|---|
| CA | 2394856 A1 | 6/2001 |

(Continued)

OTHER PUBLICATIONS

Hursting, Stephen D. et al. Calorie Restriction, Aging and Cancer Prevention: Mechanisms of Action and Applicability to Humans, Annual Review of Medicine, vol. 54, pp. 131-152, 2003.

Huttunen, R., et al., Fatal Outcome in Bacteremia is Characterized by High Plasma Cell Free DNA Concentration and Apoptotoc DNA Fragmentation: A Prospective Cohort Study, PLoS One, vol. 6, e21700, 2011.

International Search Report for PCT/RU2003/000304, dated Mar. 25, 2004.

International Search Report for PCT/RU2004/000260, dated Dec. 9, 2004.

International Search Report for PCT/RU2004/000261, dated Oct. 21, 2004.

(Continued)

*Primary Examiner* — Lisa J Hobbs
(74) *Attorney, Agent, or Firm* — Troutman Sanders LLP

(57) ABSTRACT

The invention relates to the use of a deoxyribonuclease (DNase) enzyme for prevention or amelioration of toxicity associated with various cytostatic and/or cytotoxic chemotherapeutic compounds and radiation therapy.

15 Claims, 4 Drawing Sheets

(56) References Cited

U.S. PATENT DOCUMENTS

| | | |
|---|---|---|
| 2014/0193389 A1 | 7/2014 | Genkin et al. |
| 2015/0010523 A1 | 1/2015 | Genkin et al. |
| 2015/0010527 A1 | 1/2015 | Shaaltiel et al. |
| 2015/0110769 A1 | 4/2015 | Genkin et al. |
| 2016/0130570 A1 | 5/2016 | Genkin et al. |
| 2016/0303204 A1 | 10/2016 | Genkin et al. |

FOREIGN PATENT DOCUMENTS

| | | |
|---|---|---|
| DE | 4024530 A1 | 2/1992 |
| DE | 10221194 A1 | 12/2003 |
| EP | 0325191 A2 | 7/1989 |
| EP | 1431762 A1 | 6/2004 |
| EP | 1655036 A1 | 5/2006 |
| EP | 1661579 A2 | 5/2006 |
| EP | 1666055 A1 | 6/2006 |
| EP | 1880733 A1 | 1/2008 |
| EP | 2095825 A1 | 9/2009 |
| EP | 2497488 A1 | 9/2012 |
| GB | 984464 A | 2/1965 |
| GB | 1005985 A | 9/1965 |
| IL | 199005 B | 4/2012 |
| JP | S61293927 A | 12/1986 |
| JP | 2000-229881 A | 8/2000 |
| JP | 2006-290769 A | 10/2006 |
| NZ | 299257 A | 8/2000 |
| RU | 2099080 C1 | 12/1997 |
| RU | 2202109 C1 | 4/2003 |
| RU | 2207876 C1 | 7/2003 |
| RU | 2227029 C2 | 4/2004 |
| RU | 2239404 C1 | 11/2004 |
| RU | 2239442 C1 | 11/2004 |
| RU | 2267329 C2 | 1/2006 |
| RU | 2269356 C2 | 2/2006 |
| RU | 2269357 C2 | 2/2006 |
| RU | 2269358 C2 | 2/2006 |
| RU | 2269359 C2 | 2/2006 |
| RU | 2308968 C2 | 10/2007 |
| WO | 1993/003709 A1 | 3/1993 |
| WO | 1995/00170 A1 | 1/1995 |
| WO | 1997/028266 A1 | 8/1997 |
| WO | 1997/47751 A1 | 12/1997 |
| WO | 2000/003709 A1 | 1/2000 |
| WO | 2000/031238 A2 | 6/2000 |
| WO | 2001/074905 A1 | 10/2001 |
| WO | 200182949 A2 | 11/2001 |
| WO | 2003/068254 A1 | 8/2003 |
| WO | 2005/004789 A2 | 1/2005 |
| WO | 2005/004903 A1 | 1/2005 |
| WO | 2005/004904 A1 | 1/2005 |
| WO | 2005/007187 A1 | 1/2005 |
| WO | 2005/115444 A2 | 12/2005 |
| WO | 2006/130034 A1 | 12/2006 |
| WO | 2008/039989 A2 | 4/2008 |
| WO | 2008/047364 A2 | 4/2008 |
| WO | 2008/066403 A2 | 4/2008 |
| WO | 2011/073665 A1 | 6/2011 |
| WO | 2012/075506 A2 | 6/2012 |
| WO | 2014/020564 A1 | 2/2014 |
| WO | 2017/147446 A1 | 8/2017 |

OTHER PUBLICATIONS

International Search Report for PCT/RU2004/000262, dated Oct. 21, 2004.
International Search Report for PCT/RU2005/000236, dated Nov. 24, 2005.
International Search Report for PCT/RU2006/000642, dated Aug. 2, 2007.
Irvine, D. Stewart et al., "DNA Integrity in Human Spermatozoa: Relationships with Semen Quality", Journal of Andrology (2000) vol. 21, No. 01, pp. 33-44.
Juncosa, Barbara, DNA on the Loose: Next-Gen Blood Tests Tap Free-Floating Genetic Material, Scientific American, Mar. 18, 2009.
Jylhava et al., Aging is associated with quantitative and qualitative changes in circulating cell-free DNA: the Vitality 90+ study, Mechanisms of Ageing and Development, vol. 132, pp. 20-26, 2011.
Kagan, Valerian E. et al., Toward Mechanism-based Antioxidant Interventions, Ann NY Acad Sci., vol. 959, pp. 188-198, 2002.
Kalandarishvili F., Nakoplenie spontanno povrezhdennoj DNK v ne-i postgepatjektomirovannoj pecheni u staryh krys, Med. Novosti Gruzii, No. 5, pp. 11-12, 1998 (Reference in Russian and English-language translation).
Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (Reference in Russian and English-language translation).
Kawane, K, et al., DNAse II deficiency causes chronic polyarthritis in mice, Nature Clinical Practice Rheumatology, vol. 3, No. 4, p. 192, 2007.
Kenyon, Cynthia, "A Conserved Regulatory System for Aging", Cell 2001; 105:165-168.
Krapf F, et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.
Krtolica, Ana et al., "Senescent Fibroblasts Promote Epithelial Cell Growth and Tumorigenesis: A Link Between Cancer and Aging", PNAS (2001) vol. 98, No. 21, pp. 12072-12077.
Lachmann PJ, Lupus and Desoxyribonuclease, Lupus, vol. 12, pp. 202-206, 2003.
Lecompte, et al., Detection of free-circulating tumor-associated DNA in plasma of colorectal cancer patients and its association with prognosis, Int. J. Cancer, vol. 100, pp. 542-548, 2002.
Lee, D., Continued Marketing of a Useless Drug ('Varidase') in Panama, Lancet, March, vol. 335, p. 667, 1990.
Leland et al., Cancer chemotherapy—ribonucleases to the rescue, Chem. & Bio., vol. 8, pp. 405-413, 2001.
Leon et al., Free DNA in the Serum of Cancer Patients and the Effect of Therapy, Cancer Research, vol. 37, pp. 646-650, 1977.
Li et al., The Haemophilus ducreyi cytolethal distending toxin activates sensors of DNA damage and repair complexes in proliferating and non-proliferating cells, Cellular Microbiology, vol. 4, pp. 87-99, 2002.
Liggett et al., Methylation patterns of cell-free plasma DNA in relapsing-remitting multiple sclerosis, Journal of Neurological Sciences, vol. 290, pp. 16-21, 2010.
Macanovic et al., The treatment of systemic lupus erythematosus (SLE) in NZB/W FI hybrid mice; studies with recombinant murine DNase and with dexamethasone. Clinical and Experimental Immunology (106), pp. 243-252, 1996.
Malickova, Karin et al., Decreased Activity of DNase-I Predisposes to Immune-Mediated Complications in MD Patients During Anti-TNFA Treatment, Gastroenterology, Abstract 202, vol. 138 (5 Supplement 1), S-37, 2010.
Maurer, HR, Bromelain: biochemistry, pharmacology and medical use, Cell Mol. Life. Sci., vol. 58, pp. 1234-1245, 2001.
Mel'Nikov D, et al., Voprosy onkologicheskoi pomoschi na etape reformirovaniya; zdravookhraneniya, Ekaterinburg, pp. 159-161, 1996 (Reference in Russian and English-language translation).
Merkus et al., DNase treatment for atelectasis in infants with severe respiratory syncytial virus bronchiolitis, Eur Respir J, vol. 18, pp. 734-737, 2001.
Moreira VG et al., Usefulness of cell-free plasma DNA, procalcitonin and C-reactive protein as markers of infection in febrile patients, Annals of Clinical Biochemistry, vol. 47, pp. 253-258, 2010.
Morton, C. O., et al., "Dynamics of extracellular release of Aspergillus fumigatus DNA and galactomannan during growth in blood and serum", J. Med. Microbiol. (2010) vol. 59, pp. 408-413.
Mosca et al., Cell-free DNA in the plasma of patients with systemic sclerosis, Clinical Rheumatology, vol. 28, pp. 1437-1440, 2009.
Mueller V. and Schmit J., "Fungal biodiversity: what do we know? What can we predict?" Biodivers Conserv, (2007) vol. 16, pp. 1-5.
Mutirangura A., Serum/plasma viral DNA: mechanisms and diagnostic applications to nasopharyngeal an cervical carcinoma, Ann NY Acad Sci., vol. 945, pp. 59-67, 2001.

(56) References Cited

OTHER PUBLICATIONS

National Institute on Aging, "Can We Prevent Aging? Tips from the National Institute on Aging", Feb. 2012; pp. 1-8.
Nestle & Roberts, An extracellular nuclease from Serratia marcescens, J. Biol. Chem., vol. 244, pp. 5213-5218, 1969.
Ngan et al., Remarkable Application of Serum EBV EBER-1 in Monitoring Response of Nasopharyngeal Cancer Patients to Salvage Chemotherapy, Ann. NY Acad. Sci., 945, 73-79, 2001.
Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).
Oliven et al., Orally and Rectally Administered Streptokinase, Pharmacology, vol. 22, pp. 135-138, 1981.
Osivac et al., Reorganizacija DNK i biologicheskoje starenije, Biohimija, vol. 62, pp. 1491-1502, 1997 (Reference in Russian and English-language translation).
Parrinello, Simona et al., "Stromal-epithelial Interactions in Aging and Cancer: Senescent Fibroblasts alter Epithelial Cell Differentiation", Journal of Science (2004) vol. 118, No. 03, pp. 485-496.
Perel'Man MI, et al., Molekuljarnaja medicina i lechenie tuberkuleza, Problemi tuberkuleza, No. 5, pp. 5-7, 2001 (Reference in Russian and English-language translation).
Pisetsky, D., Immune response to DNA in systemic lupus erythematosus, Isr. Med. Assoc. J., vol. 3, pp. 850-853, 2001.
Pressler T., Review of recombinant human deoxyribonuclease (rhDNase) in the management of patients with cystic fibrosis, Biologics: Targets & Therapy, vol. 2, pp. 611-617, 2008.
Prince, W.S., et al, Pharmacodynamics of recombinant human DNase I in serum, Clin Exp Immunol, vol. 113, pp. 289-296, 1998.
Pulmozyme® (dornase alfa) Inhalation Solution product leaflet, Genetech, Inc., 2005.
Rao KS and Shrivastaw KP, Studies on the synthesis and degradation of DNA in developing and old chick cerebellum, Journal of Neurochemistry, vol. 27, pp. 1205-1210, 1976.
Raz E. et al., Anti-DNA antibodies bind directly to renal antigens and induce kidney dysfunction in the isolated perfused rat kidney, J Immunol , vol. 142, pp. 3076-3082, 1989.
Riches, A.C., et al., Blood Volume Determination in the Mouse, J. Physiol., vol. 228, pp. 279-284, 1973.
Anderson, G.P., et al., "Acquired Somatic Mutations in the molecular Pathogenesis of COPD," Trends in Pharmacological Sciences, 2003, vol. 24, Issue 2, pp. 71-76.
Andreassi, M.G., "Coronary Atherosclerosis and Somatic Mutations: An Overview of the Contributive Factors for Oxidative DNA Damage," Mutation Research, 2003, vol. 543, Issue 1, pp. 67-86.
Barrett, J.P., et al., "A Systematic Review of the Antifungal Effectiveness and Tolerability of Amphotericin B Formulations," Clinical Therapeutics, 2003, vol. 25, Issue 5, pp. 1295-1320.
Beckman, J.A., et al., "Diabetes and Atherosclerosis Epidemiology, Pathophysiology, and Management," JAMA, 2002, vol. 287, No. 19, pp. 2570-2581.
Bertoni, A.G., et al., "Diabetes and the Risk of Infection-Related Mortality in the U.S.," Diabetes Care, 2001, vol. 6, Issue 6, pp. 1044-1049.
Canuto, M.M., et al., "Antifungal Drug Resistance to Azoles and Polyenes," Lancet Infectious Diseases, 2002, vol. 2, No. 9, pp. 550-563.
Čižman, M., "The Use and Resistance of Antibiotics in the Community," International Journal of Antimicrobial Agents, 2003, vol. 21, Issue 4, pp. 297-307.
Clearfield, M.B., "Statins: Balancing Benefits, Efficacy and Safety," Expert Opinion on Pharmacotherapy, 2002, vol. 3, Issue 5, pp. 469-477.
Communication Pursuant to Article 94(3) EPC Issued in European Application No. 05745412.6, dated Jun. 12, 2013, 8 pages.
Communication Extended European Search Report for European Patent Appl. No. EP12170750.9 dated Aug. 3, 2012, 4 pages.
Communication Extended European Search Report for European Patent Appl. No. EP12170757.4 dated Aug. 3, 2012, 4 pages.
Communication Pursuant to Article 94(3) EPC Issued in European Application No. 04775224.1, dated Jul. 22, 2010, 5 pages.
Communication Pursuant to Article 94(3) EPC Issued in European Application No. 04775224.1, dated Jul. 5, 2011, 4 pages.
Communication Pursuant to Article 94(3) EPC Issued in European Application No. 04748955.4, dated Jan. 11, 2011, 3 pages.
Communication Pursuant to Article 94(3) EPC Issued in European Application No. 04748955.4, dated May 21, 2010, 4 pages.
Communication Pursuant to Article 94(3) EPC Issued in European Application No. 04748955.4, dated May 23, 2011, 3 pages.
Communication Issued by the Japanese Patent Office in Japanese Application No. 2009-539202, dated Mar. 13, 2012 and English Translation Thereof, 7 pages.
Communication Supplementary European Search Report for European Patent Appl. No. EP03796243.8, dated Jan. 12, 2010, 9 pages.
Communication Supplementary European Search Report for European Patent Appl. No. EP04748955.4, dated May 19, 2009, 5 pages.
Communication Supplementary European Search Report for European Patent Appl. No. EP04775224.1, dated Oct. 28, 2009, 5 pages.
Communication Supplementary European Search Report for European Patent Appl. No. EP05745412.6, dated Jul. 10, 2009, 4 pages.
Communication Extended European Search Report for European Patent Appl. No. EP06843990.0, dated Nov. 30, 2009, 6 pages.
Communication International Preliminary Report on Patentability for PCT/RU2003/000304, dated Nov. 1, 2005, 14 pages and English Translation Thereof, 14 pages.
Communication International Preliminary Report on Patentability for PCT/RU2004/000260, dated Jan. 14, 2006 and English Translation Thereof, 12 pages.
Communication International Preliminary Report on Patentability for PCT/RU2004/000261, dated Dec. 2, 2005 and English Translation Thereof, 10 pages.
Communication International Preliminary Report on Patentability for PCT/RU2004/000262, dated Apr. 12, 2006 and English Translation Thereof.
Communication International Preliminary Report on Patentability for PCT/RU2005/000236, dated Feb. 13, 2008 and English Translation Thereof.
Communication International Preliminary Report on Patentability for PCT/RU2006/000642, dated Jul. 7, 2009 and English Translation Thereof.
Dewitt, D.E., et al., "Outpatient Insulin Therapy in Type 1 and Type 2 Diabetes Mellitus: Scientific Review," JAMA, 2003, vol. 289, No. 17, pp. 2254-2264.
Emilien, G., et al., "Pharmacological Management of Diabetes: Recent Progress and Future Perspective in Daily Drug Treatment," Pharmacology & Therapeutics, 1999, vol. 81, No. 1, pp. 37-51.
Epstein, S.E., et al., "Infection and Atherosclerosis: Potential Roles of Pathogen Burden and Molecular Mimicry," Arterioscler Thrombosis Vascular Biology, 2000, Vo. 20, No. 6, pp. 1417-1420.
Glebova, K.B., et al., "Properties of Extracellular DNA from the Cerebrospinal Fluid and Blood Plasma during Parkinson's Disease," Bulletin of Experimental Biology and Medicine, 2014, vol. 156, Issue 6, pp. 826-828.
Gould, K.L., "New Concepts and Paradigms in Cardiovascular Medicine: The Noninvasive Management of Coronary Artery Disease," The American Journal of Medicine, 1998, vol. 104, pp. 2s-17s.
Graham, R.M., "Cyclosporine: Mechanisms of Action and Toxicity," Cleaveland Clinic Journal of Medicine, 1994, vol. 61, No. 4, pp. 308-313.
Hakkim, A., et al., "Impairment of Neutrophil Extracellular Trap Degradation is Associated with Lupus Nephritis," PNAS, 2010, vol. 107, No. 21, pp. 9813-9818.
International Search Report and Written Opinion for PCT/RU2016/000284, dated Nov. 10, 2016, 3 pages.
Kadioglu, E. et al., "Detection of oxidative DNA damage in lymphocytes of patients with Alzheimer's disease", Biomarkers (2004), vol. 9, No. 2, pp. 203-209.
Li, X. et al., "Systemic Diseases Caused by Oral Infection," Clinical Microbiology Reviews, 2000, vol. 13, No. 4, pp. 547-558.

(56) References Cited

OTHER PUBLICATIONS

Moghadasian, M.H., et al., "A Safety Look at Currently Available Statins," Expert Opinion on Drug Safety, 2002, vol. 1, Issue 3, pp. 269-274.
Perl, T.M., "The Threat of Vancomycin Resistance," The American Journal of Medicine, 1999, vol. 106, Issue 5, pp. 26s-37s.
Pietropaolo, M. et al., "Evidence of Islet Cell Autoimmunity in Elderly Patients With Type 2 Diabetes", Diabetes (2000), vol. 49, pp. 32-38.
Roper, N.A., "Cause-Specific Mortality in a Population with Diabetes: South Tees Diabetes Mortality Study," Diabetes Care, 2002, vol. 25, No. 1, pp. 43-48.
Sefton, A.M., "Mechanisms of Antimicrobial Resistance," Drugs, 2002, vol. 62, Issue 4, pp. 557-566.
Shuster, A.M., et al., "DNA Hydrolyzing Autoantibodies," Science, 1992, vol. 256, Issue 5057, pp. 665-667.
Tolkoff-Rubin, N.E., et al., "Recent Advances in the Diagnosis and Management of Infection in the Organ Transplant Recipient," Seminars of Nephrology, 2000, vol. 20, No. 2, pp. 148-163.
Vijg, J., "Somatic Mutations, Genome Mosaicism, Cancer and Aging," Current Opinion in Genetics & Development, 2014, vol. 26, pp. 141-149.
Written Opinion issued International Application No. PCT/RU2015/000721 dated Aug. 18, 2016, 4 pages.
Written Opinion issued International Application No. PCT/RU2016/000284 dated Oct. 7, 2016, 5 pages.
Youssoufian, H., et al., "Mechanisms and Consequences of Somatic Mosaicism in Humans," Nature Reviews Genetics, 2002, vol. 3, pp. 748-758.
Hawes, M.C., et al., "Extracellular DNA: A Bridge to Cancer," Cancer Research, 2015, vol. 75, No. 20, pp. 4260-4264. (English Abstract Only).
International Search Report and Written Opinion for PCT/RU2015/000721, dated Aug. 25, 2016.
Martinod, K., et al., "Peptidylarginine Deiminase 4 Promotes Age-Related Organ Fibrosis," Journal of Experimental Medicine, 2017, vol. 214, No. 2, pp. 439-458.
Treshalin, I.D., et al., "Modification of antitumor drugs toxicity as a method of enhancing anticancer chemotherapeutic efficacy," Possiiskii bioterapevticheskii zhurnal, 2005, tom 4, No. 3, pp. 87-94. (English Abstract).
Robertson, D. et al. "The microbiology of the acute dental abscess", J. Med. Microbiol. (2009) vol. 58, pp. 155-162.
Roche, Pulmozyme®, Dornase alfa solution for inhalation 1.0 mg/ml, Data Sheet, 2008.
Ross, Kenneth Andrew, Evidence for somatic gene conversion and deletion in bipolar disorder, Crohn's disease, coronary artery disease, hypertension, rheumatoid arthritis, type-1 diabetes, and type-2 diabetes, BMC Medicine, vol. 9, No. 12, pp. 1-29, 2011.
Rowe P., Comhaire F. Hargreave T. Mellows H., WHO Manual for the Standardized Investigation and Diagnosis of the Infertile Couple, Cambridge University Press, 1993, 83 p.
Rowlatt, C., et al., Lifespan, Age Changes and Tumour Incidence in an Ageing C57bl Mouse Colony, Laboratory Animals, vol. 10, pp. 419-442, 1976.
Schapira, Anthony H. V., Mitochondrial disease, Lancet, vol. 368, pp. 70-82, 2006.
Schloss, Patrick D. et al., "Status of the microbial census", Microbial and Molecular Biology Reviews (2004) vol. 68, No. 04, pp. 686-691.
Schmitz, Kathryn H., et al., "The Intersection of Cancer and Aging: Establishing the Need for Breast Cancer Rehabilitation", Cancer Epidemiol Biomarkers Prey 2007; 16(5):866-872.
Scoble, J.E. et al., "Atherosclerotic renovascular disease causing renal impairment—a case for treatment," Clinical Nephrology (1989), vol. 31, No. 3, pp. 119-122.
Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).
Shah, Pallav L. et al., Medium term treatment of stable stage cystic fibrosis with recombinant human DNase I, Thorax (1995) vol. 50, pp. 333-338.
Shak et al., Recombinant human DNAse I reduces the viscosity of cystic fibrosis sputum, Proc. Natl. Acad. Sci., vol. 87, pp. 9188-9192, 1990.
Sherry et al., Presence and Significance of Desoxyribose Nucleoprotein in the Purulent Pleural Exudates of Patients, Proc, Soc. Exp. Biol. Med., pp. 179-184, 1948.
Shevchuk, NA., Vremyarazrazshenniy Immunofluorescentniy Amliz na DNK i Issieciovanie Socierzh2iniya DNK v Syvorotke Cheloveka, Voprosi Meklicinskoi Khiniii,1\io. Apr. 2001 (Reference in Russian and English Translation).
Shimony et al., Cell free DNA detected by a novel method in acute ST-elevation myocardial infarction patients, Acute Cardiac Care, vol. 12, pp. 109-111, 2010.
Sigma Product Information sheet for Deoxyribonuclease 1 from Bovine Pancreas, 2006.
Simpson G., et al., Successful treatment of empyema thoracis with human recombinant puboate deoxyribonuclease, Thorax, vol. 58, pp. 365-366, 2003.
Sugihara S., et al., Deoxyribonuclease treatment prevents blood-borne liver metastasis of cutaneously transplanted tumour cells in mice, British Journal of Cancer, vol. 67, pp. 66-70, 1993.
Supplementary European Search Report for European Patent Appl. No. EP03796243, dated Jan. 12, 2010.
Supplementary European Search Report for European Patent Appl. No. EP04748955, dated May 19, 2009.
Supplementary European Search Report for European Patent Appl. No. EP04775224, dated Oct. 28, 2009.
Supplementary European Search Report for European Patent Appl. No. EP05745412, dated Jul. 10, 2009.
Supplementary European Search Report for European Patent Appl. No. EP06843990, dated Nov. 23, 2009 and cf Form 1507.
Tetz VV and Tetz GV, Effect of Extracellular DNA Destruction by DNase I on Characteristics of Forming Biofilms, DNA and Cell Biology, vol. 29, pp. 399-405, 2010.
Tetz, GV, et al., Effect of DNase and Antibiotics on Biofilm Characteristics, Antimicrobial Agents and Chemotherapy, vol. 53, pp. 1204-1209, 2009.
Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.
Translation of PCT International Preliminary Report on Patentability for PCT/RU2003/000304, dated Nov. 1, 2005.
Translation of PCT International Preliminary Report on Patentability for PCT/RU2005/000236, dated Nov. 24, 2005.
Translation of PCT International Preliminary Report on Patentability for PCT/RU2004/000261, dated Dec. 2, 2005.
Translation of PCT International Preliminary Report on Patentability for PCT/RU2004/000260, dated Jan. 14, 2006.
Translation of PCT International Preliminary Report on Patentability for PCT/RU2004/000262, dated Apr. 12, 2006.
Translation of PCT International Preliminary Report on Patentability for PCT/RU2005/000236, dated Feb. 13, 2008.
Translation of PCT International Preliminary Report on Patentability for PCT/RU2006/000642, dated Jul. 7, 2009.
Ulrich & Friend, Toxicogenomics and drug discovery: will new technologies help us produce better drugs? Nature, vol. 1, pp. 84-88, 2002.
van der Vaart et al., Annals of the New York Academy of Science 1137:92-97, 2008.
Varidase Buccal Tablets product information from Lederle Laboratories Inc., Canad. M. A. J., vol. 84, pp. 867-868, 1961.
Varidase product information from EPGOnline, accessed on Dec. 12, 2011.

(56) References Cited

OTHER PUBLICATIONS

Vonmoos, P.L. and Straub, P.W., Absorption and hematologic effect of streptokinase-streptodornase (varidase) after intracavital or oral administration, Schweiz Med Wochenschr, vol. 109, pp. 1538-1544,1979, Abstract.
Whitchurch, et al., Extracellular DNA Required for Bacterial Biofilm Formation, Science, vol. 295, p. 1487, 2002.
Whitfield, J. F. et al., "The Effects of X-Radiation on Lactate Metabolism of Mammalian Cells", Experimental Cell Research (1965), vol. 37, pp. 637-649.
WHO Laboratory Manual for the Examination of Human Semen and Sperm-cervical Mucus Interaction, 4th ed., Cambridge University Press, 1999, 128 p.
Yastrebova N.E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).
Yasuda, Toshihiro et al., Activity Measurement for Deoxyribonucleases I and II with Picogram Sensitivity Based on DNA/SYBR Green I Fluorescence, Analytical Biochemistry, vol. 255, pp. 274-276, 1998.
Amendment filed in U.S. Appl. No. 10/619,356 dated Jun. 24, 2008, 15 pages total.
Communication issued by the Japanese Patent Office in Japanese Application No. 2009-539202, dated Feb. 22, 2013, 4 pages total.
International Search Report for PCT/GB2011/051557, dated Feb. 27, 2012, 4 pages total.
International Search Report for PCT/US2011/043290, dated Dec. 9, 2011, 2 pages total.
International Preliminary Report on Patentability issued by the International Searching Authority in International Application No. PCT/RU2015/000721, dated May 1, 2018, 5 pages total.
Ye et al., Quantification of Circulating Cell-Free DNA in the Serum of Patients with Obstructive Sleep Apnea-Hypopnea Syndrome, Lung, vol. 188, pp. 469-474, 2010.
Zaman, et al., Direct amplification of Entamoeba histolytica DNA from amoebic liver abscess pus using polymerase chain reaction, Parasitol. Res., vol. 86, pp. 724728, 2000.
Zaravinos et al., Levosimendan reduces plasma cell-free DNA levels in patients with ischemic cardiomyopathy, J. Thromb. Thrombolysis, vol. 31, pp. 180-187, 2011.
Zhong, et al., Presence of mitochondrial tRNA(leu(UUR) A to G 3243 mutation in DNA extracted from serum and plasma of patients with type A 2 diabetes mellitus. J. Clin. Pathol., vol. 53(6), pp. 466-469, 2000.
Amendment filed in U.S. Appl. No. 10/564,861 dated Jun. 24, 2008.
Anker, P. et al., "Tumor-related alterations in circulating DNA, potential for diagnosis, prognosis and detection of minimal residual disease," Leukemia, vol. 15, pp. 289-291, 2001.
Arinchina, N.I. et al., "Cellular and Humoral Mechanisms of Immunity Changing", Ageing Biology, Physiology manual (1982), pp. 280-282; including English translation thereof.
Ashton, G., "Growing pains for biopharmaceuticals," Nature Biotech, vol. 19, pp. 307-311, 2001.
Aung, K.L. et al., "Current status and future potential of somatic mutation testing from circulating free DNA in patients with solid tumours," HUGO J, vol. 4, pp. 11-21, 2010.
Beishon, M., "What can we learn from liquid biopsies? Early detection, disease prognosis, a guide to treatment, a key to unlock the secrets of how cancers evolve. Researchers have high hopes for what they can learn from the biological detritus shed by primary tumours and metastases." CancerWorld, pp. 12-17, Sep.-Oct. 2015.
Botto, N. et al., "Elevated levels of oxidative DNA damage in patients with coronary artery disease," Coronary Artery Disease, vol. 13, pp. 269-274, 2002.
Boyko, M. et al., "Cell-free DNA—a marker to predict ischemic brain damage in a rat stroke experimental model," Journal of Neurosurgical Anesthesiology, vol. 23, pp. 222-228, 2011.

Burt, M. et al., "Detection of circulating donor deoxyribonucleic acid by microsatellite analysis in a liver transplant recipient," Liver Transpl Surg., vol. 2, No. 5, pp. 391-394, 1996.
Campisi, Judith, "Cancer and Ageing: Rival Demons?" Nature Reviews/Cancer, vol. 3, pp. 339-349, 2003.
Campisi, Judith et al. "Cellular Senescence: When Bad Things Happen to Good Cells", Nature Reviews/Molecular Cell Biology, vol. 08, pp. 729-740, 2007.
Canudas-Romo, Vladimir, "Three Measures of Longevity: Time Trends and Record Values", Demography; vol. 47, No. 2, pp. 299-312, 2010.
Coppe, Jean-Philippe et al., "Secretion of Vascular Endothelial Growth Factor by Primary Human Fibroblasts at Senescence", The Journal of Biological Chemistry, vol. 281, No. 40, pp. 29568-29574, 2006.
Davis, J.C. et al., "Recombinant human Dnase I (rhDNase) in patients with lupus nephritis," Lupus, vol. 8, pp. 68-76, 1999.
Davis, Brian R. et al., "Somatic mosaicism in the Wiskott-Aldrich syndrome; Molecular and functional characterization of genotypic revertants," Clinical Immunology, vol. 135, pp. 72-83, 2010.
Dayan, A.D., "Pharmacological-Toxicological (Expert Report on Recombinant Human Deoxyribonuclease I (rhDNase; PulmozymeTM))," Hum. Exp. Toxicol., vol. 13, pp. S2-s42,1994.
Deitsch, K.W. et al., "Transformation of malaria parasites by the spontaneous uptake and expression of DNA from human erythrocytes," Nucleic Acids Research, vol. 29, No. 3, pp. 850-853, 2001.
Deocharan, B. et al., Alpha-actinin is a cross-reactive renal target for pathogenic anti-DNA antibodies, J. Immunol., vol. 168, pp. 3072-3078, 2002.
Department of Health and Human Services Food and Drug Administration, Federal Register, vol. 50, No. 240, Friday, Dec. 13, 1985, Part II, excerpt from p. 51104.
Dittmar, Manuela et al., "A novel mutation in the DNASE1 gene is related with protein instability and decreased enzyme activity in thyroid autoimmunity," Journal of Autoimmunity, vol. 32, pp. 7-13, 2009.
El Hassan, N. et al., "Rescue use of Dnase in critical lung atelectasis mucus retention in premature neonates," Pediatrics., vol. No. 2, pp. 468-470, 2001.
Erickson, Robert P., "Somatic gene mutation and human disease other than cancer," Mutation Research, vol. 543, pp. 125-136, 2003.
Erickson, Robert P., "Somatic gene mutation and human disease other than cancer: An update," Mutation Research, vol. 705, pp. 96-106, 2010.
European Office Action, dated Jun. 12, 2013, which issued during the prosecution of European Patent Application No. 05745412.6, which corresponds to the present application.
Extended European Search Report for European Patent Appl. No. EP12170750 dated Aug. 3, 2012.
Extended European Search Report for European Patent Appl. No. EP12170754 dated Aug. 3, 2012.
Extended European Search Report for European Patent Appl. No. EP12170757 dated Aug. 3, 2012.
Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).
Finlay, B.J., "The global diversity of protozoa and other small species," International Journal for Parasitology, vol. 28, pp. 29-48, 1998.
Freshney, R. I., Culture of Animal Cells, A Manual of Basic Technique, Alan R. Liss, Inc., 1983, New York, pp. 3-4.
Funakoshi, A, et al., "Clinical Investigation of Serum Deoxyribonuclease: II. Clinical Studies of Serum Deoxyribonuclease Activity in Pancreatic Disease," Gastroenterologia Japonica, vol. 14, No. 5, pp. 436-440, 1979.
Gal, S. et al., "Detection and Quantitation of Circulating Plasmodium falciparum DNA by Polymerase Chain Reaction", Methods in Molecular Biology, vol. 336, pp. 155-162, 2006.
Gannushikina, I.V., et al., "Plasma DNA Levels in Patients with Atherosclerotic Involvement of the Major Arteries of the Head and lateral Amyotrophic Sclerosis," Bulletin of Experimental Biology and Medicine, vol. 124, No. 12, pp. 1164-1166, 1997 (Translated

(56) References Cited

OTHER PUBLICATIONS from: Gannushkina IV. et al., Uroven DNK v plazme krovi bolnykhs aterosklerotichskim porazheniem magistralnykh artery golovy i bokovym amiotroficheskim sklerozom, Byulleten' Experimental'noi Biologii i Meditsiny, Moscow, Meditsina, No. 12, pp. 610-612,1997).

Gibbs, J.B. et al., "Mechanism-Based Target Identification and Drug Discovery in Cancer Research," Science, vol. 287, pp. 1969-1973, 2000.

Gibson, R. L. et al., "Pathophysiology and management of pulmonary infections in cystic fibrosis.", Am J. Respir Crit Care Med, vol. 168, pp. 918-951, 2003.

Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 13-28, 2126, 1996 (Reference in Russian and English-language translation of pp. 14-17 and 20-27).

Gormally, E. et al., "Circulating free DNA in plasma or serum as biomarker of carcinogenesis: Practical aspects and biological significance," Mutation Research, vol. 635, pp. 105-117, 2007.

Gorrini, C. et al., Effect of apoptogenic stimuli on colon carcinoma cell lines with a different c-myc expression level, Int J Mol Med, vol. 11, pp. 737-742, 2003.

Gura, T., "Systems for identifying New Drugs Are Often Faulty," Science, vol. 278, pp. 1041-1042, 1997.

Hann, B. et al., "Building 'validated' mouse models of human cancer." Curr Opin Cell Biol, vol. 13, No. 6, pp. 778-784, 2001.

Harley, Calvin B., "Telomere Loss: Miotic Clock or Genetic Time Bomb?" Mutation Research, vol. 256, pp. 271-282, 1991.

Hayflick, L. et al. "The Serial Cultivation of Human Diploid Cell Strains1", Experimental Cell Research, vol. 25, pp. 585-621, 1961.

Hayflick, L., "The Limited in Vitro Lifetime of Human Diploid Cell Strains," Experimental Cell Research, vol. 37, pp. 614-636, 1965.

Hayflick, L., "Aging Under Glass", Dept. of Medical Microbiology, Stanford University School of Medicine, Exp. Geront., vol. 5, pp. 291-303,1970.

Holterhus, Paul-Martin et al., "Mosaicism due to a Somatic Mutation of the Androgen Receptor Gene Determines Phenotype in Androgen Insensitivity Syndrome," Journal of Clinical Endocrinology and Metabolism, vol. 82, No. 11, pp. 3584-3589, 1997.

Horlitz, Martin et al., "Optimized Quantification of Fragmented, Free Circulating DNA in Human Blood Plasma Using a Calibrated Duplex Real-Time PCR," PLoS One, vol. 4, Issue 9, e7207, 2009.

Communication (Extended European Search report) issued by the Europe Patent Office in European application No. 15907392.3 dated May 24, 2019, 8 pages total.

Esposito, S. et al., "The Place of Desoxyribonuclease in the Treatment of Chronic Lymphatic Leukemia" Database EMBASE, Elsevier Science Publishers (1972) 1 page total.

Mittal, B. et al., "Effect of Recombinant Human Deoxyriboneclease on Oropharyngeal Secretions in Patients with Head-and-Neck Cancers Treated with Radiochemotherapy" International Journal of Radiation Onocology Biology Physics (2013) vol. 87, No. 2, pp. 282-289.

Anunobi, R. et al., "Extracellular DNA Promotes Colorectal Tumor Cell Survival after Cytotoxic Chemotherapy" Journal of Surgical Research (2018) vol. 226, pp. 181-191.

Foote, M., "The Importance of Planned Dose of Chemotherapy on Time: Do We Need to Change our Clinical Practice?" The Oncologist: Physician Education (1998) vol. 3, pp. 365-368.

Lelbach, A. et al., "Current Perspectives of Catabolic Mediators of Cancer Cachexia" Med Sci Monit (2007) vol. 13, No. 9, pp. RA168-RA173.

Meirovitz, A. et al., "Novel Formation of Rnase and DNAse Employing Unique Nanospheres to Allow Oral Drug Delivery and Demonstrate Anticancer Activity" ASCO University (2015) Abstract, 2 pages total.

Mittra, I. et al., "Prevention of Chemotherapy Toxicity by Agents that Neutralize or Degrade Cell-Free Chromatin" Annals of Oncology (2017) vol. 28, pp. 2119-2127.

Petruzzelli, M. et al., "Mechanisms of Metabolic Dysfunction in Cancer-Associated Cachexia" Genes & Development (2016) vol. 30, pp. 489-501.

Communication (Japanese Notice of Grounds for Rejection) issued by the Japanese Patent Office in Japanese Application No. 2018-519282, dated Jun. 27, 2019, 9 pages total.

Kanyshkova, TG et al., "Multiple enzymic activities of human milk lactoferrin" European Journal of Biochemistry (2003) vol. 270, No. 16, pp. 3353-3361.

A.

B.

METHOD TO IMPROVE SAFETY AND EFFICACY OF ANTI-CANCER THERAPY

CROSS-REFERENCE TO RELATED APPLICATIONS

This application claims priority to U.S. Provisional Application Ser. No. 62/014,341, filed on Jun. 19, 2014, which is herein incorporated by reference in its entirety.

FIELD OF THE INVENTION

The invention relates to the use of deoxyribonuclease (DNase) enzyme for prevention or amelioration of toxicity associated with various cytostatic and/or cytotoxic chemotherapeutic compounds and radiation therapy.

BACKGROUND OF THE INVENTION

Cancers are a very significant cause of death in humans. The leading cancer therapies today are surgery, radiation and cytostatic and/or cytotoxic chemotherapy. Despite of advances in the field of chemotherapy treatments, most of the known chemotherapies are associated with serious side effects including myelopathy, hematopathy, digestive disorders (e.g., nausea, vomiting, anorexia, diarrhea, constipation), pulmonary insufficiency, dermatopathy, nervous system disorders, endocrine disorders, genital disorders, cardiovascular disorders, hepatopathy, pancreatic disorder, nephropathy, bladder trouble, hyperuricemia, decrease of immunocompetence, infections, hypersensitivity to light, hair loss, etc. (2-5). These side effects are life threatening or seriously debilitating and cause significant chemotherapy-related morbidity and mortality.

One of the major complications of cancer chemotherapy is damage to bone marrow cells or suppression of their function. Specifically, chemotherapy damages or destroys hematopoietic precursor cells, primarily found in the bone marrow and spleen, impairing the production of new blood cells (granulocytes, lymphocytes, erythrocytes, monocytes, platelets, etc.). Many cancer patients die of infection or other consequences of hematopoietic failure subsequent to chemotherapy. Chemotherapeutic agents can also result in subnormal formation of platelets, which produces a propensity toward hemorrhage. Inhibition of erythrocyte production can result in anemia. It has been also recently recognized that development of more potent cytotoxic therapies and more effective chemotherapy regimens for a wider range of malignancies significantly increases the frequency of a serious toxic adverse event termed Tumor Lysis Syndrome (TLS) (16). TLS is a group of metabolic complications that can occur as a result of administration of cytotoxic therapies, most often in the context of chemotherapy for lymphomas and leukemias, and are caused by the breakdown products of dying cells.

The main reason chemotherapy is so debilitating and the symptoms so severe is that chemotherapeutic drugs are often unable to differentiate between normal, healthy cells and tumor cells they are designed to target. Another mechanism responsible for chemotherapy-related toxicity is toxic effects of cellular components released from cells undergoing necrosis or apoptosis as result of chemotherapy-induced cell death.

The side effects associated with chemotherapeutic drugs limit the frequency and dosage at which such drugs can be administered leading to lower efficacy.

As the concept of systemic cytotoxic chemotherapy has evolved, a lot of research efforts have been spent to identify possible approaches to attenuate chemotherapy-related toxicity and avoid the cessation of the patients' exposure to chemotherapeutic agents. Chemotherapeutic dosing and schedule modulation leading to the development of less toxic dosing modalities is one possibility (6). Others have proposed dietary approaches, such as fasting or restricting specific nutrients during and after chemotherapy (7), and supplementation of the patient's diet with several specific dietary amino acids (8). The use of certain drug-specific metabolic antidotes, particularly acylated derivatives of uridine or cytidine, for the prevention of toxicity induced by pyrimidine nucleoside analogs is disclosed in U.S. Pat. No. 7,776,838. Use of chromanol glycoside for prevention of toxicity induced by alkylating agents is disclosed in U.S. Pat. No. 7,462,601. Use of antioxidants for prevention of anthracycline-induced cardiotoxicity has also been proposed (9). Attenuation of tissue-specific toxicity of chemotherapeutic drugs, in particular prevention of mucositis using topical application of alpha-interferon or beta-interferon (U.S. Pat. No. 5,017,371); prevention of stomach and bowel side effect using selective glucagon-like-peptide-2 (GLP-2) analogues (U.S. Pat. No. 8,642,727) prevention of liver damage using A2B adenosine receptor antagonist (U.S. Pat. No. 8,188,099), and prevention of prostate damage using inhibitor of IGFBP-1 growth factor (U.S. Pat. No. 8,211,700) has been also disclosed. Use of alkaline phosphatase enzyme to ameliorate general toxicity of chemotherapy and to maintain healthy muscle and adipose tissue mass in mammals receiving chemotherapy has been disclosed in U.S. Pat. No. 8,460,654.

Development of new compositions and methods for preventing or ameliorating chemotherapy-related toxicity is highly desired.

Current radiotherapies for treatment of cancers provide significant benefits for patients with early stage and radiosensitive cancers, but these benefits are much less significant for patients with radioresistant tumors (e.g., brain or pancreas cancers) and for patients with late stage tumors. For these patients, the radiation needed to eradicate the tumor can cause intolerable or fatal radiation damage. This is especially the case for pediatric patients, whose rapidly developing normal tissues are often more radiosensitive than their tumors, and who therefore cannot tolerate radiotherapy that would be curative for adults with the same disease. Damage to normal tissue limits the use of radiotherapy treatments for cancer patients of a young age, patients with central nerve system cancers, radioresistant cancers, and late stage cancer with large tumors.

Development of new compositions and methods for preventing or ameliorating radiotherapy-related toxicity is highly desired.

SUMMARY OF THE INVENTION

As specified in the Background Section, there is a great need in the art to develop new compositions and methods for preventing or ameliorating chemotherapy- and radiotherapy-related toxicity. The present invention addresses this and other needs by providing compositions and methods based on DNase enzyme.

Specifically, in one aspect, the invention provides a method for preventing or ameliorating a toxicity associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate at least one side effect of said chemotherapy. In another aspect, the invention provides a method for increasing efficacy of a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate at least one side effect of said chemotherapy and wherein the DNase administration results in prevention or amelioration of toxicity associated with said chemotherapy.

In one specific embodiment of the above methods, said side effect of said chemotherapy is selected from the group consisting of body weight loss, bone marrow toxicity, catabolic changes in blood biochemistry, myocardial necrosis, gastrointestinal toxicity, suppression of immunity, and neutropenia.

In a further aspect, the invention provides a method for preventing or ameliorating a catabolic state leading to body weight loss associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate the catabolic state leading to body weight loss associated with said chemotherapy. In one specific embodiment, the chemotherapy is anthracycline-containing therapy.

In yet another aspect, the invention provides a method for preventing or ameliorating a bone marrow toxicity and/or catabolic changes in blood biochemistry associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate the bone marrow toxicity and/or catabolic changes in blood biochemistry associated with said chemotherapy. In one specific embodiment, the chemotherapy is anthracycline-containing therapy.

In a further aspect, the invention provides a method for preventing or ameliorating a cardiotoxicity associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate the cardiotoxicity associated with said chemotherapy. In one specific embodiment, the cardiotoxicity is myocardial necrosis. In one specific embodiment, the chemotherapy is anthracycline-containing therapy.

In another aspect, the invention provides a method for preventing or ameliorating a gastrointestinal toxicity associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate the gastrointestinal toxicity associated with said chemotherapy. In one specific embodiment, the chemotherapy is 5 fluorouracil- and/or etoposide-containing therapy.

In yet another aspect, the invention provides a method for preventing or ameliorating a suppression of immunity associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate the suppression of immunity associated with said chemotherapy. In one specific embodiment, the chemotherapy is taxane-containing therapy.

In a further aspect, the invention provides a method for preventing or ameliorating neutropenia associated with a cytostatic and/or cytotoxic chemotherapy in a subject suffering from a cancer and receiving or deemed to receive said chemotherapy, which method comprises administering to the subject a therapeutically effective amount of a DNase enzyme, wherein said amount of the DNase enzyme is effective to prevent or ameliorate neutropenia associated with said chemotherapy. In one specific embodiment, the chemotherapy is cyclophosphamide-containing therapy.

In one embodiment of any of the above methods of the invention, the chemotherapy comprises administration of one or more compounds selected from the group consisting of antimetabolites, alkylating agents, anticancer antibiotics, microtubule-targeting agents, topoisomerase inhibitors, alkaloids, and targeted therapeutics.

In one embodiment of any of the above methods of the invention, the chemotherapy comprises administration of one or more compounds selected from the group consisting of anthracycline, doxorubicin, 5-fluorouracil (5-FU), etoposide, taxane, and cyclophosphamide.

In one embodiment of any of the above methods of the invention, the DNase enzyme is administered during a cycle of the chemotherapy. In another embodiment of any of the above methods of the invention, the DNase enzyme is administered after a cycle of the chemotherapy.

In another aspect, the invention provides a method for preventing or ameliorating a toxicity associated with a radiation therapy in a subject suffering from a cancer and receiving said radiation therapy, which method comprises administering to the subject a therapeutically effective amount of a DNase enzyme, wherein said amount of the DNase enzyme is effective to prevent or ameliorate at least one side effect of said radiation therapy.

In a further aspect, the invention provides a method for increasing the efficacy of a radiation therapy in a subject suffering from a cancer and receiving said radiation therapy, which method comprises administering to the subject a therapeutically effective amount of a DNase enzyme, wherein said amount of the DNase enzyme is effective to prevent or ameliorate at least one side effect of said radiation therapy and wherein the DNase administration results in prevention or amelioration of toxicity associated with said radiation therapy.

In one embodiment of the above two methods, the side effect of the radiation therapy is selected from the group consisting of skin irritation or damage, fatigue, nausea, vomiting, fibrosis, bowel damage, memory loss, infertility, and a second cancer.

In yet another aspect, the invention provides a method for preventing or ameliorating a body weight loss associated with a radiation therapy in a subject suffering from a cancer and receiving said radiation therapy, which method comprises administering to the subject a therapeutically effective amount of a DNase enzyme, wherein said amount of the DNase enzyme is effective to prevent or ameliorate body weight loss associated with said radiation therapy.

In one embodiment of the above three methods, the radiation therapy is external beam radiation therapy or systemic radioisotope therapy.

In one embodiment of the above three methods, the DNase enzyme is administered during a cycle of the radiation therapy. In another embodiment, the DNase enzyme is administered after a cycle of the radiation therapy.

In one embodiment of any of the above methods of the invention, the DNase enzyme is DNase I (e.g., human recombinant DNase I or bovine pancreatic DNase I) or an analogue thereof (e.g., DNase X, DNase gamma, or DNA-SIL2). In another embodiment of any of the above methods of the invention, the DNase enzyme is DNase II. In one embodiment, the DNase enzyme has an extended half-life (e.g., is conjugated with polysialic acid or is protected from binding to actin by modification of actin binding-site).

In one embodiment of any of the above methods of the invention, the therapeutically effective amount of a DNase enzyme is at least 0.5 mg/kg/day or at least 1000 Kunitz units (KU)/kg/day, preferably at least 1.5 mg/kg/day or at least 3000) KU/kg/day. In one embodiment of any of the above methods of the invention, the therapeutically effective amount of a DNase enzyme is from 0.5 to 100 mg/kg/day or from 1000 to 200000 KU/kg/day, preferably from 0.5 to 50 mg/kg/day or from 1000 to 100000 KU/kg/day, more preferably from 1.5 to 50 mg/kg/day or from 3000 to 100000 KU/kg/day, most preferably from 10 to 50 mg/kg/day or from 20000 to 10000) KU/kg/day.

In one embodiment of any of the above methods of the invention, the DNase enzyme is administered intravenously or intraperitoneally. In one embodiment of any of the above methods of the invention, the DNase enzyme is administered enterally (e.g., orally).

In one embodiment of any of the above methods of the invention, the subject is human.

These and other aspects of the present invention will be apparent to those of ordinary skill in the art in the following description, claims and drawings.

DETAILED DESCRIPTION OF THE INVENTION

Figure 1:
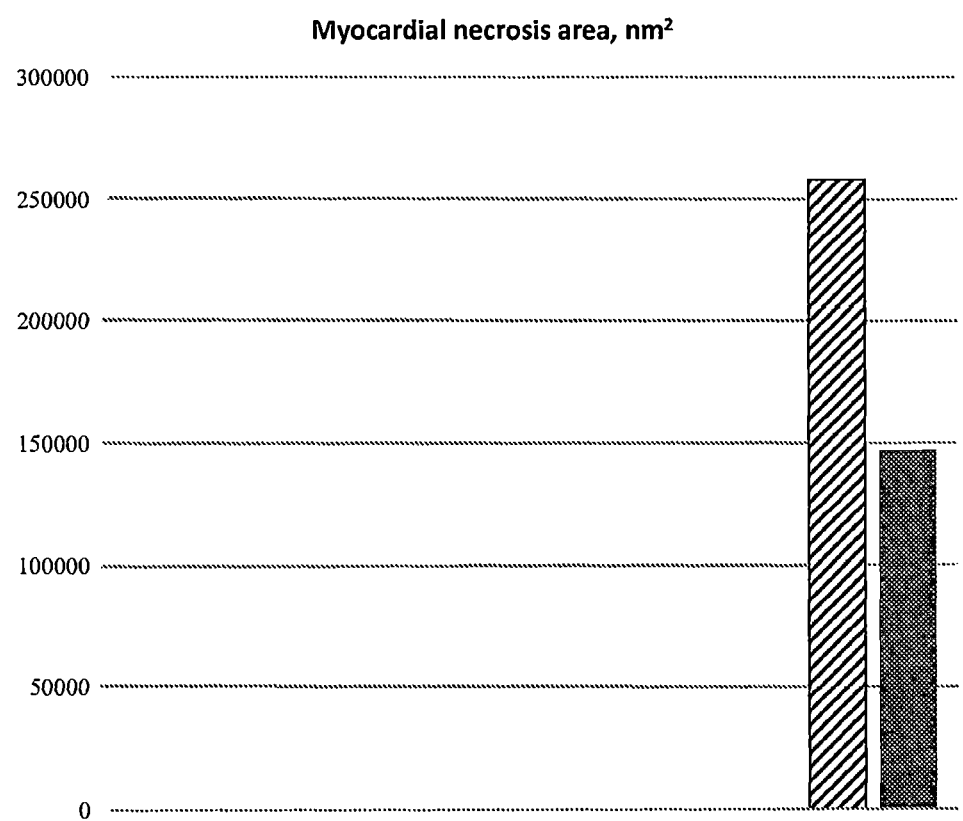
FIG. 1 is a bar graph showing myocardial necrosis area in deceased rats challenged with sub-lethal IV doses of doxorubicin (7.5 mg/kg) and either daily IP injections of human recombinant DNase I (15 mg/kg) (black bar) or daily LP injections of placebo (WFI) (diagonal hatched bar). Serial myocardium microscopy samples from each heart were analyzed using an automated video analyzer to quantify the necrotic areas. The sum of necrotic area ($S_{na}$; $nm^2$) was calculated as a sum of necrotic areas in 30 serial slides from each individual autopsied heart (n=3 for DNase I-treated rats—black bar; n=5 for placebo-treated rats—diagonal hatched bar).

The present inventors have previously demonstrated that deoxyribonuclease (DNase) enzyme is a useful agent for treating cancer (see. e.g., U.S. Patent Appl. Pub. No. 2010/0150903 and U.S. Pat. No. 7,612,032), a property which has been recently confirmed by several authors (10-12). However, it has been also reported that DNase lacks a significant influence on tolerability of antiproliferative chemotherapy (15) and can even significantly contribute to increase in toxicity of chemotherapy (17).

The present invention is based on an unexpected discovery by the inventors that DNase enzymes not only increase efficacy of cytostatic and/or cytotoxic chemotherapy, but also significantly decrease the chemotherapy-related toxicity. This discovery is especially surprising in light of prior reports on lack of DNase influence on tolerability of chemotherapy (15) and DNase contribution to increase in nephrotoxicity of chemotherapy (17). The ability of DNase to prevent and/or ameliorate chemotherapy-related toxicity is shared by different types of DNase enzymes and is drug- and tissue-independent making DNases highly desirable and potent candidates for chemotherapy accessory therapy. Indeed, as demonstrated in the Examples section, below, various types of DNase enzymes (e.g., DNase I. DNase gamma, and DNase II) can be used to ameliorate toxicity of such diverse types of chemotherapeutic agents as Doxorubicin (anthracycline antibiotic which works by intercalating DNA), 5-FU (antimetabolite which works through inhibition of thymidylate synthase), Etoposide (topoisomerase inhibitor), Taxane (microtubule disruptor), and Cyclophosphamide (alkylating agent).

Definitions

The terms "cytostatic and/or cytotoxic chemotherapy" and "chemotherapy" are used interchangeably herein to refer to a therapy involving administering of a cytostatic and/or cytotoxic agent.

The terms "anti-cancer agent" and "anti-cancer chemotherapeutic agent" are used herein to refer to any chemical compound, which is used to treat cancer. Anti-cancer chemotherapeutic agents are well known in the art (see, e.g., Gilman A. G., et al., The Pharmacological Basis of Therapeutics, 8th Ed., Sec 12:1202-1263 (1990)). Specific examples of chemotherapeutic agents are provided throughout the specification.

The term "side effect of a chemotherapy" as used herein refers to an undesirable and unintended, although not necessarily unexpected, result of a chemotherapy.

As used herein, the terms "radiotherapy", "radiation therapy", and "RT" are used interchangeably to refer to the medical use of ionizing radiation as part of a cancer treatment to damage the DNA of malignant cells, either directly or by creating charged particles within the affected cells that damage the DNA. Commonly used types of radiation therapy encompassed by the present invention include, e.g., external beam radiation therapy (EBRT or XRT), brachytherapy/sealed source radiation therapy, and systemic radioisotope therapy/unsealed source radiotherapy The terms "side effect of a radiotherapy" or "side effect of a radiation therapy" as used herein refer to an undesirable and unintended, although not necessarily unexpected, result of a radiation therapy. Which side effects develop depend on the area of the body being treated, the dose given per day, the total dose given, the patient's general medical condition, and other treatments given at the same time, and may include, e.g., skin irritation or damage, fatigue, nausea, vomiting, fibrosis, bowel damage, memory loss, infertility, or a second cancer.

The term "catabolic state" as used herein refers to a condition characterized by a rapid weight loss and loss of fat and skeletal muscle mass, which may occur in a background of chemotherapy or chemoradiation therapy. Associated clinical events include, for example, immunosuppression, muscle weakness, predisposition to pulmonary embolism, thrombophlebitis, and altered stress response.

As used herein, the terms "deoxyribonuclease" and "DNase" are used to refer to any enzyme that catalyzes the hydrolytic cleavage of phosphodiester linkages in the DNA backbone. A wide variety of deoxyribonucleases is known and can be used in the methods of the present invention. Non-limiting examples of DNases useful in the methods of the present invention include, e.g., DNase I (e.g., human recombinant DNase I or bovine pancreatic DNase I), analogues of DNase I (such as, e.g., DNase X, DNase gamma, and DNASIL2), DNase II, phosphodiesterase I, lactoferrin, and acetylcholinesterase. Also encompassed by the present invention are DNase enzymes which have an extended half-life (e.g., DNase enzymes conjugated with polysialic acid or protected from binding to actin by modification of actin binding-site; see, e.g., Gibson et al., (1992) J. Immunol. Methods, 155, 249-256). DNase I cleaves DNA preferentially at phosphodiester linkages adjacent to a pyrimidine nucleotide, yielding 5'5'-phosphate-terminated polynucleotides with a free hydroxyl group on position 3', on average producing tetranucleotides. DNase I acts on single-stranded DNA, double-stranded DNA, and chromatin.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to 5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. For example, in connection with cancer the term "treat" may mean eliminate or reduce a patient's tumor burden, or prevent, delay or inhibit metastasis, etc.

As used herein the term "therapeutically effective" applied to dose or amount refers to that quantity of a compound or pharmaceutical composition that is sufficient to result in a desired activity upon administration to a subject in need thereof. Within the context of the present invention, when the term "therapeutically effective" is used in connection with the use of deoxyribonuclease (DNase) to ameliorate or prevent side effects of a cytostatic and/or cytotoxic chemotherapy, it refers to an amount of DNase or a pharmaceutical composition containing DNase that is effective to ameliorate or prevent at least one side effect of such cytostatic and/or cytotoxic chemotherapy. Note that when a combination of active ingredients is administered (e.g., a combination of DNase and another compound effective for ameliorating or preventing side effects of chemotherapy) the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a subject (e.g., a mammal such as a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "targeted therapeutics" is used to refer to a class of chemical and biological compounds that may be effective in patients whose cancers have a specific molecular target, but they may not be effective in the absence of such a target (18).

As used herein, the term "subject" refers to any mammal. In a preferred embodiment, the subject is human.

As used in this specification and the appended claims, the singular forms "a," "an," and "the" include plural references unless the context clearly dictates otherwise.

In accordance with the present invention there may be employed conventional pharmacology and molecular biology techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M J. Gait ed. 1984); Nucleic Acid Hybridization (B. D. Hames & S. J. Higgins eds. (1985)); Transcription and Translation (B. D. Hames & S. J. Higgins, eds. (1984)): *Animal Cell Culture* (R. I. Freshney, ed. (1986>>; *Immobilized Cells and Enzymes* (IRL Press, (1986)); B. Perbal, *A Practical Guide To Molecular Cloning* (1984); F. M.

Ausubel et al. (eds.), *Current Protocols in Molecular Biology*. John Wiley & Sons, Inc. (1994); among others.

Therapeutic Methods of the Invention

In one aspect, the invention provides a method for preventing or ameliorating a toxicity associated with a cytostatic and/or cytotoxic chemotherapy in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate at least one side effect of said chemotherapy.

In a further aspect, the invention provides a method for increasing the efficacy of a cytostatic and/or cytotoxic chemotherapy in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate at least one side effect of said chemotherapy and wherein the DNase administration results in prevention or amelioration of toxicity associated with said chemotherapy.

According to the present invention, DNase enzymes can be used to ameliorate toxicity of a wide range of different chemotherapeutic agents. Non-limiting examples of such agents include anti-metabolites such as pyrimidine analogs (e.g., 5-fluorouracil [5-FU], floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as vinca alkaloids (e.g., vinblastine, vincristine, and vinorelbine), microtubule disruptors such as taxanes (e.g., paclitaxel, docetaxel), vincristin, vinblastin, nocodazole, epothilones and navelbine, epidipodophyllotoxins (e.g., etoposide, teniposide), DNA damaging agents (e.g., actinomycin, amsacrine, anthracyclines, bleomycin, busulfan, camptothecin, carboplatin, chlorambucil, cisplatin, nedaplatin, cyclophosphamide, cytoxan, dactinomycin, daunorubicin, doxorubicin, epirubicin, aclarubicin, purarubicin, hexamethylmelamine oxaliplatin, iphosphamide, melphalan, mechlorehtamine, mitomycin, mitoxantrone, nitrosourea, nimustine, ranimustine, estramustine, plicamycin, procarbazine, taxol, taxotere, teniposide, triethylenethiophosphoramide and etoposide (VP16)); antibiotics (e.g., dactinomycin (actinomycin D), daunorubicin, doxorubicin (adriamycin), idarubicin, anthracyclines, mitoxantrone, bleomycins, plicamycin (mithramycin), pleomycin, peplomycin, mitomycins (e.g., mitomycin C), actinomycins (e.g., actinomycin D), zinostatinstimalamer); enzymes (e.g., L-asparaginase); neocarzinostatin; antiplatelet agents; antiproliferative/antimitotic alkylating agents such as nitrogen mustards (e.g., mechlorethamine, cyclophosphamide and analogs, imidazol carboxamide, melphalan, chlorambucil, nitrogen mustard-N-oxide hydrochloride, ifosfamide), ethylenimines and methylmelamines (e.g., hexamethylmelamine, thiotepa, carboquone, triethylene thiophosphar-
amide), alkyl sulfonates (e.g., busulfan, isoprosulfan tosylate), nitrosoureas (e.g., carmustine (BCNU) and analogs, streptozocin), trazenes-dacarbazinine (DTIC); epoxide type compounds (e.g., mitobronitol); antiproliferative/antimitotic antimetabolites such as folic acid analogs (e.g., methotrexate); platinum coordination complexes (e.g., cisplatin, carboplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); antisecretory agents (e.g., brefeldin); immunosuppressives (e.g., cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blockers; nitric oxide donors; antisense oligonucleotides; antibodies (e.g., trastuzumab); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, mitoxantrone, topotecan, irinotecan); growth factor signal transduction kinase inhibitors; mitochondrial dysfunction inducers; chromatin disruptors; sobuzoxane; tretinoin; pentostatin; flutamide; porphimer natrium; fadrozole; procarbazine; aceglatone; radioimmunotherapy (RIT) compounds (e.g., Ibritumomab tiuxetan, Iodine ($^{131}$I) tositumomab); and targeted radionuclide therapy (TRT) compounds (e.g., samarium-153-EDTMP, strontium-89-chloride).

Non-limiting examples of side effects of cytostatic and/or cytotoxic chemotherapy which can be prevented or ameliorated by administering DNase enzymes according to the methods of the invention include, for example, bone marrow toxicity, neutropenia, myelopathy (e.g., leukopenia, granulocytopenia, lymphopenia, thrombocytopenia, crythropenia); hematopathy (e.g., plasma fibrinogenopenia); catabolic changes in blood biochemistry; gastrointestinal disorders (e.g., nausea, vomiting, anorexia, body weight loss, heavy feeling of stomach, diarrhea, constipation, stomatitis, esophagitis); pulmonary insufficiency (e.g., chronic pneumonia, lung fibrosis, ARDS, ALS, lung emboli); dermatopathy (e.g., keratinization, pachymenia, chromatosis, epilation, rash, nail alternation, cancer-induced alopecia); nervous system disorders (e.g., paresthesia, depression, deep areflexia, neuroparalysis, auditory disorder, allolalia, disorientation, neurologic manifestation, cerebellar ataxia, somnolence, coma, vertigo, frequency of micturition, frequency of defecation desire); endocrine disorders (e.g., pituitary disorder, adrenal disorder, hyperglycemia, hypoglycemia); genital disorders (e.g., hyposexuality, oligospermia, gynecomastia, menstrual disorder); cardiovascular disorders (e.g., myocardial necrosis, cardiomyopathy, arrhythmia, low blood pressure, tachycardia, cardiac failure); hepatopathy, pancreatic disorder, nephropathy, bladder trouble, hyperuricemia, decrease of immunocompetence, and infection.

In another aspect, the invention provides a method for preventing or ameliorating a toxicity associated with a radiation therapy in a subject suffering from a cancer and receiving said radiation therapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate at least one side effect of said radiation therapy.

In a further aspect, the invention provides a method for increasing the efficacy of a radiation therapy in a subject suffering from a cancer and receiving said radiation therapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate at least one side effect of said radiation therapy and wherein the DNase administration results in prevention or amelioration of toxicity associated with said radiation therapy.

According to the present invention, DNase enzymes can be used to ameliorate toxicity and increase efficacy of various types of radiation therapy, including, for example, external beam radiation therapy (EBRT or XRT), brachytherapy/sealed source radiation therapy, and systemic radioisotope therapy/unsealed source radiotherapy.

Non-limiting examples of side effects of radiotherapy which can be prevented or ameliorated by administering DNase enzymes according to the methods of the invention include, for example, skin irritation or damage, fatigue, nausea, vomiting, fibrosis, bowel damage, memory loss, infertility, and a second cancer.

The methods of the invention can be used in subjects suffering from a broad range of cancers, which subjects are subjected to anti-cancer chemotherapeutic treatments which result in deleterious side effects. Non-limiting examples of relevant cancers include, e.g., breast cancer, prostate cancer, multiple myeloma, transitional cell carcinoma, lung cancer (e.g., non-small cell lung cancer (NSCLC)), renal cancer, thyroid cancer, leukemia (e.g., chronic myeloid leukemia, acute myeloid leukemia, chronic lymphocytic leukemia, acute lymphocytic leukemia), lymphoma (e.g., B cell lymphoma. T cell lymphoma, non-Hodgkins lymphoma, Hodgkins lymphoma), head and neck cancer, esophageal cancer, stomach cancer, colon cancer, intestinal cancer, colorectal cancer, rectal cancer, pancreatic cancer, liver cancer, cancer of the bile duct, cancer of the gall bladder, ovarian cancer, uterine endometrial cancer, vaginal cancer, cervical cancer, bladder cancer, neuroblastoma, sarcoma, osteosarcoma, malignant melanoma, squamous cell cancer, bone cancer, including both primary bone cancers (e.g., osteosarcoma, chondrosarcoma, Ewing's sarcoma, fibrosarcoma, malignant fibrous histiocytoma, adamantinoma, giant cell tumor, and chordoma) and secondary (metastatic) bone cancers, soft tissue sarcoma, basal cell carcinoma, angiosarcoma, hemangiosarcoma, myxosarcoma, liposarcoma, osteogenic sarcoma, angiosarcoma, endotheliosarcoma, lymphangiosarcoma, lymphangioendotheliosarcoma, synovioma, testicular cancer, uterine cancer, gastrointestinal cancer, mesothelioma, leiomyosarcoma, rhabdomyosarcoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, choriocarcinoma, seminoma, embryonal carcinoma, Wilms' tumor, epithelial carcinoma, glioma, glioblastoma, astrocytoma, medulloblastoma, craniopharyngioma, ependymoma, pinealoma, hemangioblastoma, acoustic neuroma, oligodendroglioma, meningioma, retinoblastoma, medullary carcinoma, thymoma, sarcoma, etc.

In one embodiment, the invention provides a method for preventing or ameliorating a catabolic state leading to body weight loss associated with a cytostatic and/or cytotoxic chemotherapy (e.g., doxorubicin therapy) in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate catabolic state leading to body weight loss associated with said chemotherapy.

In another embodiment, the invention provides a method for preventing or ameliorating bone marrow toxicity and/or catabolic changes in blood biochemistry associated with cytostatic and/or cytotoxic chemotherapy (e.g., doxorubicin therapy) in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate bone marrow toxicity and/or catabolic changes in blood biochemistry associated with said chemotherapy.

In yet another embodiment, the invention provides a method for preventing or ameliorating cardiotoxicity (e.g., myocardial necrosis) associated with a cytostatic and/or cytotoxic chemotherapy (e.g., doxorubicin therapy) in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate cardiotoxicity associated with said chemotherapy.

In a further embodiment, the invention provides a method for preventing or ameliorating gastrointestinal toxicity associated with a cytostatic and/or cytotoxic chemotherapy (e.g., 5-fluorouracil/etoposide combination chemotherapy) in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate gastrointestinal toxicity associated with said chemotherapy.

In another embodiment, the invention provides a method for preventing or ameliorating suppression of immunity associated with a cytostatic and/or cytotoxic chemotherapy (e.g., taxane therapy) in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate suppression of immunity associated with said chemotherapy.

In a further embodiment, the invention provides a method for preventing or ameliorating neutropenia associated with a cytostatic and/or cytotoxic chemotherapy (e.g., cyclophosphamide therapy) in a subject suffering from a cancer and receiving or deemed to receive said chemotherapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate neutropenia associated with said chemotherapy.

In yet another embodiment, the invention provides a method for preventing or ameliorating a body weight loss associated with a radiation therapy in a subject suffering from a cancer and receiving said radiation therapy, which method comprises administering to the subject a therapeutically effective amount of a DNase enzyme (e.g., DNase I (e.g., human recombinant DNase I or bovine pancreatic DNase I), analogues of DNase I (such as, e.g., DNase X, DNase gamma, or DNASIL2), DNase II, phosphodiesterase I, lactoferrin, or acetylcholinesterase), wherein said amount of the DNase enzyme is effective to prevent or ameliorate body weight loss associated with said radiation therapy.

In one embodiment of any of the above methods, the therapeutically effective amount of a DNase enzyme is at least 0.5 mg/kg/day or at least 1000 Kunitz units (KU)/kg/day, preferably at least 1.5 mg/kg/day or at least 3000 KU/kg/day. In one embodiment of any of the above methods, the therapeutically effective amount of a DNase enzyme is from 0.5 to 100 mg/kg/day or from 1000 to 200000 KU/kg/day, preferably from 0.5 to 50 mg/kg/day or from 1000 to 10000 KU/kg/day, more preferably from 1.5 to 50 mg/kg/day or from 3000 to 100000 KU/kg/day, most preferably from 10 to 50 mg/kg/day or from 20000 to 10000 KU/kg/day.

In one embodiment of any of the methods of the invention, the subject is human.

Methods for Administering DNase and DNase Compositions

In the methods of the invention, a DNase enzyme can be administered before, during, and/or after the administration of a chemotherapeutic agent or during or after the administration of a radiation therapy. Preferably, (i) a DNase enzyme and a chemotherapeutic agent (or a radiation therapy) are administered at the same time, and/or (ii) a DNase enzyme is administered shortly after the administration of a chemotherapeutic agent (or a radiation therapy). DNase can be administered to the patient at one time or over a series of treatments; once or several times per day.

DNase doses useful in the methods of the invention depend on the type of chemotherapy or radiation therapy side effects to be treated, the severity and course of these side effects, previous therapy, the patient's clinical history and response to chemotherapy (or radiation therapy) and DNase, as well as the discretion of the attending physician. Non-limiting examples of useful dosage ranges include from 0.5 to 100 mg/kg/day or from 1000 to 200000 KU/kg/day, preferably from 0.5 to 50 mg/kg/day or from 1000) to 1000 Kunitz units (KU)/kg/day, more preferably from 1.5 to 50 mg/kg/day or from 3000) to 10000 KU/kg/day, most preferably from 10 to 50 mg/kg/day or from 20000 to 100000 KU/kg/day.

The administration of a DNase enzyme according to the methods of the invention can be performed by any suitable route, including systemic administration as well as administration directly to the site of the disease (e.g., to a primary tumor). Specific non-limiting examples of useful routes of administration include intravenous (IV), subcutaneous (SC), intraperitoneal (IP), oral, or by inhalation.

In certain embodiments, a DNase enzyme is formulated in a pharmaceutical composition with a pharmaceutically acceptable carrier or excipient.

The formulations used in the methods of the invention may conveniently be presented in unit dosage form and may be prepared by methods known in the art. The amount of active ingredients that can be combined with a carrier material to produce a single dosage form will vary depending upon the host being treated and the particular mode of administration. The amount of active ingredients that can be combined with a carrier material to produce a single dosage form will generally be that amount of the compound which produces a therapeutic effect.

In general, the formulations can be prepared with a liquid carrier, or a finely divided solid carrier, or both, and then, if necessary, shaping the product.

Pharmaceutical compositions suitable for parenteral administration may comprise one or more active ingredients (a DNase and, optionally, another compound effective for ameliorating or preventing side effects of a cytostatic and/or cytotoxic chemotherapy or a radiation therapy) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms can be made by forming microencapsule matrices of one or more active ingredients in biodegradable polymers such as polylactide-polyglycolide. Depending on the ratio of active ingredient to polymer, and the nature of the particular polymer employed, the rate of active ingredient's release can be controlled. Examples of other biodegradable polymers include poly(orthoesters) and poly(anhydrides). Depot injectable formulations are also prepared by entrapping the active ingredients in liposomes or microemulsions which are compatible with body tissue.

Formulations for oral administration can be in the form of capsules, cachets, pills, tablets, powders, granules, or as a solution or a suspension in an aqueous or non-aqueous liquid (e.g., as a mouthwash, as a composition to be swallowed, or as an enema), or as an oil-in-water or water-in-oil liquid emulsion, and the like, each containing a predetermined amount of one or more active ingredients.

In solid dosage forms for oral administration (capsules, tablets, pills, dragees, powders, granules, and the like), one or more active ingredients can be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate: (8) absorbents, such as kaolin and bentonite clay; (9) lubricants, such a talc, calcium stearate, magnesium stearate, solid polyethylene glycols, sodium lauryl sulfate, and mixtures thereof: and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Suspensions, in addition to one or more active ingredients, can contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Powders and sprays can contain, in addition to one or more active ingredients, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Amelioration of Acute Doxorubicin Toxicity in Rats

Materials and Methods

42 Wistar male rats (180-200 g) were used in this experiment (obtained from Stolbovaya nursery of Russian Academy of Medical Sciences). Animals were kept under standard conditions with free access to food and drinking water. Animals were randomized into 7 groups (6 animals in each group) as follows:
1. Group I: control group (no Doxorubicin, no DNase);
2. Group II: animals treated by daily intravenous (IV) injections of Doxorubicin (LENS) at 3.75 mg/kg/day dose for 5 days plus daily intraperitoneal (IP) injections of human recombinant DNase I (Pharmsynthez OJSC) at 15 mg/kg/day dose (30000 KU/kg/day); Doxorubicin and DNase I injections were administered at the same time;
3. Group III: animals treated by daily IV injections of Doxorubicin (LENS) at 3.75 mg kg/day dose for 5 days plus daily IP injections of placebo (water for injection [WFI];
4. Group IV: animals treated by daily IV injections of Doxorubicin (LENS) at 7.5 mg/kg/day dose for 5 days plus daily IP injections of human recombinant DNase I (Pharmsynthez OJSC) at 15 mg/kg/day dose (30000 KU/kg/day); Doxorubicin and DNase I injections were administered at the same time;
5. Group V: animals treated by daily IV injections of Doxorubicin (LENS) at 7.5 mg/kg/day dose for 5 days plus daily IP injections of placebo (WFI);
6. Group VI: animals treated by daily IV injections of Doxorubicin (LENS) at 10.0 mg/kg/day dose for 5 days plus daily IP injections of human recombinant DNase I (Pharmsynthez OJSC) at 15 mg/kg/day dose (30000 KU/kg/day); Doxorubicin and DNase I injections were administered at the same time;
7. Group VII: animals treated by daily IV injections of Doxorubicin (LENS) at 10.0 mg/kg/day dose for 5 days plus daily IP injections of placebo (WFI).

Animals were monitored during 2 weeks from the beginning of experiment for survival and weight.

Results

TABLE 1

Animal survival data among different experimental groups

| | Group | | | | | | |
|---|---|---|---|---|---|---|---|
| | I | II | III | IV | V | VI | VII |
| Number of dead/out of total in group | 0/6 | 1/6 | 3/6 | 3/6 | 5/6 | 6/6 | 6/6 |
| Median survival of deceased rats (in days) | — | 7 | 12 ± 2.1 | 10.3 ± 1.4 | 8.2 ± 1.0 | 6.2 ± 1.0 | 6.6 ± 0.9 |

The results summarized in Table 1 demonstrate that DNase suppresses the lethality of doxorubicin and increases the life span of rats challenged with sub-lethal doses of doxorubicin. The suppression of lethality, as measured by the number of surviving animals, occurred in a dose-dependent manner.

TABLE 2

Body weight of surviving rats (in grams) following doxorubicin administration at 3.75 mg/kg dose, measured before administration of doxorubicin and on Days 4, 7, and 14 of the treatment.

|  | Group I | Group II | Group III |
|---|---|---|---|
| Baseline | 167 ± 4 | 168 ± 4 | 164 ± 6 |
| Day 4 | 165 ± 5 | 160 ± 6 | 143 ± 6 |
| Day 7 | 172 ± 4 | 158 ± 5 | 151 ± 7 |
| Day 14 | 175 ± 4 | 164 ± 6 | 156 ± 6 |

The results summarized in Table 2 demonstrate that DNase treatment ameliorates body weight loss in rats who survived an acute doxorubicin challenge at the $LD_{50}$ dose of 3.75 mg/kg.

TABLE 3

Blood cell counts and blood biochemistry data from surviving rats following doxorubicin administration at 3.75 mg/kg dose on Day 14 of treatment.

|  | Group I | Group II | Group III |
|---|---|---|---|
| Haemoglobin, G % | 13.5 ± 0.5 | 11.9 ± 0.4 | 9.5 ± 0.7 |
| Hematocrit, % | 42.2 ± 2.1 | 37.5 ± 2.0 | 30.5 ± 2.2 |
| RBC, $10^{12}$/L | 7.8 ± 0.2 | 6.8 ± 0.2 | 5.7 ± 0.4 |
| RBC sedimentation count, mm/h | 4.4 ± 0.3 | 16.5 ± 0.8 | 24.1 ± 4.5 |
| Platelets, $10^9$/L | 540 ± 25 | 440 ± 25 | 340 ± 25 |
| WBC $10^9$/L | 7.7 ± 0.4 | 6.0 ± 0.3 | 4.9 ± 0.2 |
| Segmented neutrophils, % | 29.6 ± 1.3 | 13.5 ± 1.0 | 11.6 ± 1.3 |
| Basophils, % | 0 | 0 | 0 |
| Eosinophils, % | 0 | 0 | 2.4 ± 0.3 |
| Monocyte, % | 2.7 ± 0.5 | 2.9 ± 0.4 | 2.3 ± 0.5 |
| Lymphocytes, % | 63.4 ± 1.7 | 80.3 ± 1.4 | 82.3 ± 2.2 |
| Plasmatic cells, % | 0.3 ± 0.1 | 0.3 ± 0.1 | 1.3 ± 0.5 |
| Protein, g/L | 74.2 ± 4.3 | 64.3 ± 5.2 | 54.7 ± 7.3 |
| Urea, mmol/L | 4.12 ± 0.21 | 5.39 ± 0.40 | 7.21 ± 0.3 |
| Creatinine, μmol/L | 54.7 ± 6.2 | 65.5 ± 7.2 | 68.3 ± 8.4 |
| Glucose, mmol/L | 6.8 ± 0.1 | 5.9 ± 0.2 | 6.1 ± 0.2 |
| Total lipids, g/L | 2.22 ± 0.20 | 2.12 ± 0.21 | 2.06 ± 0.27 |
| Total cholesterol, mmol/L | 1.32 ± 0.30 | 1.69 ± 0.18 | 1.10 ± 0.29 |
| Total bilirubin, mmol/L | 8.9 ± 0.3 | 9.5 ± 0.5 | 8.2 ± 0.6 |
| Bilirubin bound, mmol/L | 2.0 ± 0.4 | 2.6 ± 0.3 | 2.0 ± 0.5 |
| Na, mmol/L | 142 ± 3 | 151 ± 4 | 144 ± 2 |
| K, mmol/L | 5.2 ± 0.2 | 5.1 ± 0.3 | 5.6 ± 0.3 |

The results summarized in Table 3 indicate that DNase treatment ameliorates bone marrow toxicity and catabolic changes in blood biochemistry in rats who survived an acute doxorubicin challenge at the $LD_{50}$ dose of 3.75 mg/kg.

The hearts deceased rats challenged with sub-lethal doses of doxorubicin (7.5 mg/kg) from (Groups IV and V) were autopsied. Serial myocardium microscopy samples from each heart were analyzed using an automated video analyzer to quantify the necrotic areas. The sum of necrotic area ($S_{na}$; $nm^2$) was calculated as a sum of necrotic areas in 30 serial slides from each individual autopsied heart (n=3 for Group IV (FIG. 1, black bars); n=5 for Group V (FIG. 1, diagonal hatched bars)). Group IV received daily IP injections of human recombinant DNase I at 15 mg/kg dose, while Group V received daily IP injections of placebo (WFI).

The results presented in FIG. 1 demonstrate that DNase treatment decreases the myocardial necrosis area in rats challenged with sub-lethal doses of doxorubicin.

Example 2: Amelioration of Gastrointestinal Toxicity of 5-Fluorouracil/Etoposide Combination Chemotherapy Materials and Methods 64 male Wistar rats (170-200 g) were used in this experiment (obtained from Stolbovaya nursery of Russian Academy of Medical Sciences). Animals were kept under standard conditions with free access to food and drinking water. On Day 1, Etoposide (LANCE) 200 mg/kg and 5-fluorouracil (5-FU; EBEWE) 400 mg/kg were given orally via feeding needle in 500 μl of a 9% glucose solution. Animals were divided into 4 groups of 16 rats each. Two hours after the Etoposide/5-FU challenge, rats were treated as follows:
1. Group I: IV placebo (WFI);
2. Group II: human recombinant DNase I (Pharmsynthez OJSC) at 1.5 mg/kg (3000 KU/kg) dose IV;
3. Group III: human recombinant DNase I (Pharmsynthez OJSC) at 50 mg/kg (100000 KU/kg) dose IV;
4. Group IV: cimetidine solution (Gedeon Richter) at 50 mg/kg dose IV.

36 hours later, all animals were euthanized and their stomachs were removed and analyzed for the presence of erosions and hemorrhages using an automated video analyzer system.

Results

TABLE 4

Effects of DNase I or cimetidine administration on gastrointestinal lesions in animals treated with 200 mg/kg Etoposide and 400 mg/kg 5-FU.

| Gr. | Number of animals | Chemo | Treatment | Total number of lesions per group | Median number of lesions | Number of lesion free animals |
|---|---|---|---|---|---|---|
| I | 16 | Etoposide 200 mg/kg + 5-FU 400 mg/kg per os | Placebo | 86 | 5.38 ± 1.41 | 4 (25%) |
| II | 16 | Etoposide 200 mg/kg + 5-FU 400 mg/kg per os | rHuDNase I 1.5 mg/kg IV | 60 | 3.75 ± 1.53 | 5 (31.25%) |
| III | 16 | Etoposide 200 mg/kg + 5-FU 400 mg/kg per os | rHuDNase I 50 mg/kg IV | 16 | 1.00 ± 0.69 | 12 (75%) |
| IV | 16 | Etoposide 200 mg/kg + 5-FU 400 mg/kg per os | Cimetidine 50 mg/kg IV | 40 | 2.5 ± 1.1 | 10 (62.5%) |

The results summarized in Table 4 demonstrate that DNase suppresses chemotherapy-induced ulceration and increases the number of gastrointestinal erosion-free animals in a dose-dependent manner in animals treated with etoposide and 5-FU. DNase I dose of 50 mg/kg was significantly superior in terms of achieved protection, as compared to both the 1.5 mg/kg DNaseI dose and 50 mg/kg dose of cimetidine.

Figure 2:
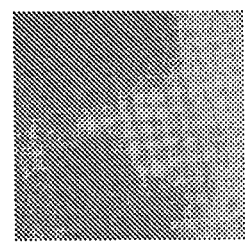
FIGS. 2A-B show the photographs of stained stomachs of rats treated with oral Etoposide (200 mg/kg) and 5-fluorouracil (5-FU; 400 mg/kg) followed either by (A) IV treatment with human recombinant DNase I (50 mg/kg) or by (B) IV placebo (WFI). Multiple erosions and ulcers are visible in the stomach in panel (B), while the stomach in panel (A) does not have any macroscopic abnormalities.
Figure 2:
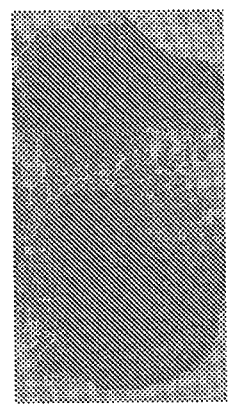

FIG. 2 shows the stained stomach of a rat from Group III (A) and a rat from Group I (B). Multiple erosions and ulcers are visible in the stomach of the Group I animal, while the stomach from the Group III animal does not have any macroscopic abnormalities.

Example 3: Amelioration of Taxane-Induced Suppression of Immunity

Materials and Methods 10 male 6-week-old (CBAxCS7Bl6) F1 mice (obtained from Rappolovo animal house) were given a single 20 mg/kg dose of paclitaxel (Paclitaxel-Teva) IV. A group of 5 paclitaxel treated mice were injected IP 1 hour later with recombinant mouse DNase gamma (USCN Life Science Inc.) at 2 mg/kg dose IP. A group of 5 untreated mice were injected IP at the same time with 1 ml of placebo (WFI) to serve as the control. All mice were killed 24 hours later by cervical dislocation. The thymuses from each group were collected and homogenized in a separator in RPMI 1640 media supplemented with 10% fetal calf serum. The suspension of thymocytes was filtered and sedimented in a centrifuge at 400×g for 2 minutes and then resuspended with the same media. Thymocytes were plated into 96 well plates (900,000 cells per well in 200 µl of RPMI 1640 supplemented with 10% fetal calf serum (FCS)) and incubated for 32 hours at 37° C., 100% humidity and 5% $CO_2$ atmosphere. Each well was then supplemented with $^3H$ thymidine (1 µCi/10 µl/well) and Concanavalin A (ConA; 50 µl: 1.25 µg/ml). After 24 hours of further incubation, thymocytes were harvested and dried. Labeled $^3H$ thymidine incorporation was measured using a Beckman scintillation counter. The data on Con A-induced lymphocyte blast transformation is summarized in Table 5, below.

Results

TABLE 5

Effect of DNase gamma on Con A-induced lymphocyte blast transformation.

| Group | Scintillation counts; CPM | |
|---|---|---|
| | Basal $^3HT$ incorporation | Con A-induced $^3HT$ incorporation |
| Control | 641 ± 62 | 7894 ± 1067 |
| Paclitaxel | 277 ± 21 | 1686 ± 142 |
| Paclitaxel + DNase | 357 ± 25 | 5237 ± 1232 |

The results summarized in Table 5 demonstrate that DNase ameliorates taxane-induced suppression of thymocytes' proliferative activity.

Example 4: Amelioration of Cyclophosphamide-Induced Neutropenia

Materials and Methods 30 female 10-12 week old BALB/C mice (obtained from Rappolovo animal house) were used in this experiment. Animals were kept under standard conditions with free access to food and drinking water. On Day 1, neutropenia was induced by a single IP injection of 200 mg/kg cyclophosphamide (Cyclophosphanum-LANS) in 200 µl of WFI. Starting on Day 2, mice were then treated as follows:
1. Group I (n=10): control (no treatment);
2. Group II (n=10): animals were treated with human recombinant DNase I (Pharmsynthez OJSC) at 25 mg/kg/day (50000 KU/kg/day) dose injected IV on Days 2-5;
3. Group III (n=10): animals were treated with human recombinant GM-CSF (Neostim, Pharmsynthez OJSC) at 200 µg/kg/day dose injected subcutaneously (SC) on Days 2-5.

The white blood cell count (WBC) in each animal was monitored daily during the 10 day experiment using blood cell counter.

Results

Figure 3:
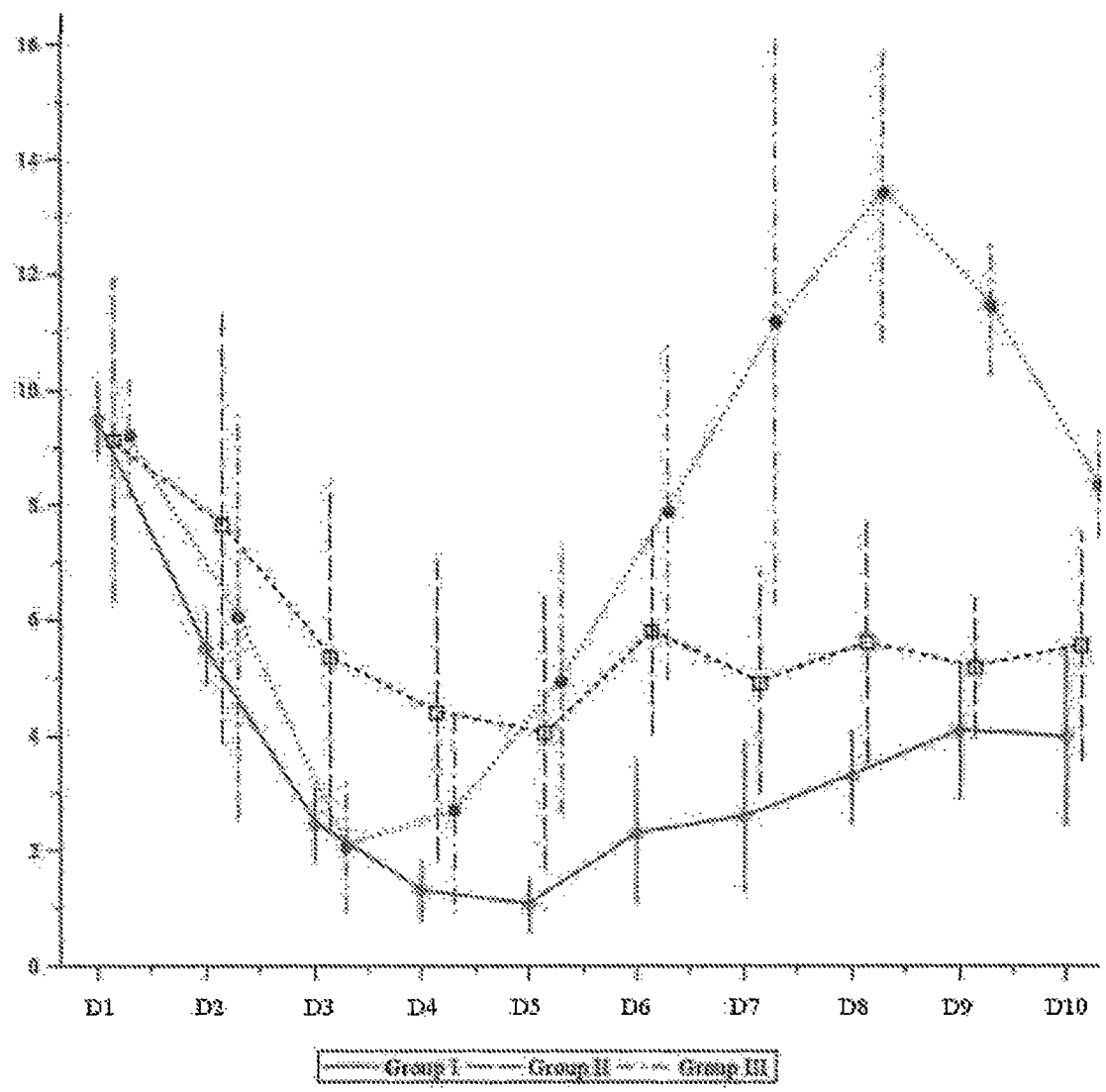
FIG. 3 is a graph summarizing the dynamics of the white blood cell count (WBC) in the three experimental groups, in which neutropenia was induced by a single IP injection of cyclophosphamide (200 mg/kg) followed by no treatment (Group I) or IV treatment with human recombinant DNase I (25 mg/kg) (Group II) or SC treatment with human recombinant GM-CSF (200 μg/kg) (Group III). The vertical axis represents WBC with units of 10 WBC/L. The horizontal axis represents the number of days after cyclophosphamide injection. The figure demonstrates the ameliorating effect of DNase treatment on neutropenia induced by an alkylating agent such as cyclophosphamide.

The graph in FIG. 3 summarizes the dynamics of the white blood cell count (WBC) in the three experimental groups. The vertical axis represents WBC with units of $10^9$ WBC/L. The horizontal axis represents the number of days after cyclophosphamide injection.

The results in FIG. 3 demonstrate that DNase ameliorates neutropenia induced by an alkylating agent such as cyclophosphamide. Of particular importance is that DNase treatment prevents the typical early phase decline in WBC count, while GM-CSF treatment is not able to prevent it.

Example 5: Synergy Between DNase Treatment and Anticancer Chemotherapy

Materials and Methods

To evaluate a possible synergy of combined use of DNase and nucleoside analog chemotherapeutic agent cytosine arabinoside (AraC), DBA2 mice (8-10 weeks old; 24-26 g; obtained from Rappolovo animal house) were transplanted IP with L1210 leukemia cells ($1\times10^5$ cells per mice; cells obtained from Petrov Institite of Oncology collection) on Day 0 to induce cancer. Treatment with DNase and AraC was initiated on Day 1 of experiment. Cytosine arabinoside (AraC; Cytosar, Pfizer) was injected IP at a dose of 1000 mg/kg on Days 2, 5 and 8. The injected doses were considered adequate for the model and injection route based on prior experiments (13-14). DNase II (Wornington) was injected IP at doses of 15 mg/kg/day and 45 mg/kg/day on Days 1, 3, 5, 8, 10, 12, 15, 17, and 19.

Animals were randomized into 6 experimental groups of 6 mice per group as follows:
1. Group I: negative control (no treatment);
2. Group II: positive control (animals treated with AraC);
3. Group II: animals treated with AraC and 15 mg/kg DNase;
4. Group IV: animals treated with AraC and 45 mg/kg DNase;
5. Group V: animals treated with 15 mg/kg DNase, no AraC;
6. Group VI: animals treated with 45 mg/kg DNase, no AraC.

Results

Figure 4:
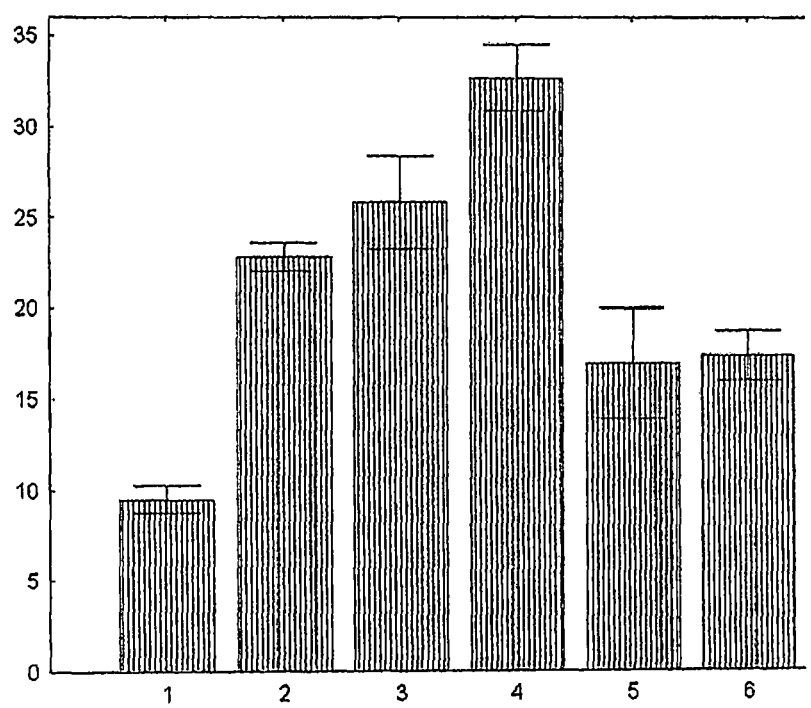
FIG. 4 is a bar graph showing a summary of survival data for animals transplanted with L1210 leukemia cells to induce cancer followed by treatment with cytosine arabinoside (AraC) and/or DNase II. The six experimental groups are represented on the horizontal axis: 1. Negative Control; 2. AraC (positive control); 3. AraC+DNase II (15 mg/kg); 4. AraC+DNase II (45 mg/kg); 5. DNase II (15 mg/kg); 6. DNase II (45 mg/kg). The figure demonstrates the synergistic effects of DNase and AraC treatment on survival rates of mice with leukemia.

Survival data are summarized in FIG. 4. The vertical axis of FIG. 4 represents the survival measured in days after implantation with the L1210 leukemia cells. The six experimental groups are represented on the horizontal axis: 1—Negative Control; 2—AraC (positive control); 3—AraC+DNase II 15 mg/kg; 4—AraC+DNase II 45 mg/kg; 5—DNase II 15 mg/kg 6—DNase II 45 mg/kg.

The results summarized in FIG. 4 show that treatment with both AraC alone (Group II) and DNase II alone (Groups V and VI) results in better survival rates versus non-treated mice (Group I). However, the combination of AraC and DNase results in a clear survival advantage over either treatment alone. The synergistic effect of the combination treatment on survival rates was dose-dependent on increasing doses DNase.

Example 6: DNase Treatment Increases Efficacy and Decreases Toxicity of Cancer Radiotherapy Materials and Methods To evaluate a possible synergy of combined use of DNase and radiation therapy, 60 SHR mice (12-14 weeks old; 28-32 g; obtained from Rappolovo animal house) were transplanted IP with Erlich carcinoma cells ($1 \times 10^6$ cells per mice; cells obtained from Petrov Institite of Oncology collection) on Day 0 to induce ascites tumor growth. Radiotherapy was performed using a cobalt-60 teletherapy machine. The abdominal fields of the mice were treated by external irradiation. The fractionation was 200 cGy per day for 5 days. Mice were divided into 6 groups treated as follows: Group 1: radiotherapy only (external irradiation 200) cGy per day for 5 days); Group 2: recombinant human DNAse I (Pharmsynthez) 20 mg/kg/day administered intramuscularly in 2 daily doses; Group 3: recombinant human DNAse I (Pharmsynthez) 40 mg/kg/day administered intramuscularly in 2 daily doses; Group 4: radiotherapy (external irradiation 200 cGy per day for 5 days) plus recombinant human DNAse I (Pharmsynthez) 20 mg/kg/day administered intramuscularly in 2 daily doses; Group 5: radiotherapy (external irradiation 200 cGy per day for 5 days) plus recombinant human DNAse I (Pharmsynthez) 40 mg/kg/day administered intramuscularly in 2 daily doses. Group 6 was a control group receiving placebo (water for injection).

Results

Animal survival and dynamics of body weight on day 16 after transplantation of Erlich carcinoma are summarized in Table 6:

| Experimental Group | % Survival on Day 16 | Change in Median Body Weight on Day 16 |
|---|---|---|
| Group 1 | 40 | −3 g |
| Group 2 | 40 | +2 g |
| Group 3 | 50 | +1.5 g |
| Group 4 | 80 | 0 |
| Group 5 | 100 | +1.5 g |
| Group 6 | 0 | +5.5 g |

The results summarized in Table 6 show that treatment with both radiation therapy alone (Group I) and DNase I alone (Groups 2 and 3) results in better survival rates versus non-treated mice (Group 6). However, the combination of radiation therapy and DNase results in a clear survival advantage over either treatment alone. The synergistic effect of the combination treatment on survival rates was dose-dependent on increasing doses of DNase. DNase treatment also clearly prevents the body weight loss induced by radiotherapy.

REFERENCES

1. Joshi et al., 2007, J. Neurosci. Res. 85:497-503.
2. Curigliano G. et al., Ann Oncol. 2012; 23 Suppl 7; vii155-vii166.
3. Syvak L. A. et al., Lik Sprava. 2012; (3-4):25-30.
4. Verstappen C. C. et al., Drugs. 2003; 63(15):1549-1563.
5. Lyman G. H. et al., Oncology (Williston Park). 2006; 20(14 Suppl 9):16-25.
6. Romiti A. et al., Cancer Chemother Pharmacol. 2013; 72(1):13-33.
7. Laviano A. et al., N Engl J Med. 2012; 366:2319-2320.
8. Gaurav K., Indian J of Med Paed Oncol., 2012; 33(1): 13-20.
9. Vincent D. T. et al., Cancer Chemother Pharmacol. 2013; 72(6): 1157-68.
10. Fushi W. et al., Cancer Res. 2013; 73:4256.
11. Cools-Lartigue J. et al., J Clin Invest. 2013; 123(8): 3446-3458.
12. Trejo-Becerril C. et al., PLoS One. 2012; 7(12): e52754.
13. Chabot, G. and Momparier, R. L., Cancer. Treat. Rep. 1984; 68:1483-1487.
14. Lech-Maranda, E. et al., Haematologica, 2000; 85:588-594.
15. Hall I H, et al., J Pharm Sci. 1974; 63(4): 625-6.
16. McBride A., et al, J Hematol Oncol. 2012; 5:75
17. Basnakian et al., J. Am. Soc. Nephrol. 2005; 16: 697-702
18. Gerber D., Am Fam Physician, 2008; 77(3):311-319

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for ameliorating a toxicity associated with a cytostatic and/or cytotoxic chemotherapy in a subject suffering from a cancer and receiving or deemed to receive said chemotherapy, which method comprises administering to the subject a therapeutically effective amount of a DNase I enzyme, wherein said amount of the DNase I enzyme is effective to ameliorate at least one side effect of said chemotherapy, wherein said side effect of said chemotherapy is selected from the group consisting of body weight loss, bone marrow toxicity, catabolic changes in blood biochemistry, cardiotoxicity, gastrointestinal toxicity, suppression of immunity, and neutropenia.

2. The method of claim 1, wherein said amount of the DNase I enzyme is effective to increase efficacy of a cytostatic and/or cytotoxic chemotherapy in the subject.

3. The method of claim 1, wherein the chemotherapy comprises administration of one or more compounds selected from the group consisting of antimetabolites, alkylating agents, anticancer antibiotics, microtubule-targeting agents, topoisomerase inhibitors, alkaloids, and targeted therapeutics.

4. The method of claim 1, wherein the chemotherapy comprises administration of one or more compounds selected from the group consisting of anthracycline, doxorubicin, 5-fluorouracil (5-FU), etoposide, taxane, cytosine arabinoside (AraC), and cyclophosphamide.

5. The method of claim 1, wherein the DNase I enzyme is administered during or after a cycle of the chemotherapy.

6. The method of claim 1, wherein the DNase I enzyme is human recombinant DNase I.

7. The method of claim 1, wherein the DNase I enzyme has an extended half-life.

8. The method of claim 1, wherein the therapeutically effective amount of the DNase I enzyme is within the range 0.5-50 mg/kg/day.

9. The method of claim 8, wherein the therapeutically effective amount of the DNase I enzyme is within the range 1.5-50 mg/kg/day.

10. The method of claim 9, wherein the therapeutically effective amount of the DNase I enzyme is within the range 10-50 mg/kg/day.

11. The method of claim 1, wherein the DNase I enzyme is administered intravenously.

12. The method of claim 1, wherein the DNase I enzyme is administered intraperitoneally.

13. The method of claim 1, wherein the DNase I enzyme is administered enterally.

14. The method of claim 1, wherein the subject is human.

15. The method of claim 1, further comprising monitoring changes in said at least one side effect of said chemotherapy after DNase I administration.

* * * * *